United States Patent
Pandit et al.

(10) Patent No.: US 11,535,873 B2
(45) Date of Patent: Dec. 27, 2022

(54) PRODUCTION OF GLYCOLATE FROM ETHYLENE GLYCOL AND RELATED MICROBIAL ENGINEERING

(71) Applicant: THE GOVERNING COUNCIL OF THE UNIVERSITY OF TORONTO, Toronto (CA)

(72) Inventors: Aditya Vikram Pandit, Toronto (CA); Radhakrishnan Mahadevan, Toronto (CA)

(73) Assignee: THE GOVERNING COUNCIL OF THE UNIVERSITY OF TORONTO, Toronto (CA)

( * ) Notice: Subject to any disclaimer, the term of this patent is extended or adjusted under 35 U.S.C. 154(b) by 26 days.

(21) Appl. No.: 16/645,621

(22) PCT Filed: Sep. 6, 2018

(86) PCT No.: PCT/CA2018/051081
§ 371 (c)(1),
(2) Date: Mar. 9, 2020

(87) PCT Pub. No.: WO2019/046946
PCT Pub. Date: Mar. 14, 2019

(65) Prior Publication Data
US 2020/0277635 A1    Sep. 3, 2020

Related U.S. Application Data

(60) Provisional application No. 62/555,431, filed on Sep. 7, 2017, provisional application No. 62/597,510, filed on Dec. 12, 2017.

(51) Int. Cl.
*C12P 7/42*       (2006.01)
*C12N 1/20*       (2006.01)

(52) U.S. Cl.
CPC .................. *C12P 7/42* (2013.01); *C12N 1/20* (2013.01); *C12N 2500/02* (2013.01); *C12N 2510/00* (2013.01)

(58) Field of Classification Search
CPC ......... C12P 7/42; C12N 1/20; C12N 2500/02; C12N 2510/00; C12Y 101/05; C12Y 101/01; C12Y 101/03; C12Y 102/01
See application file for complete search history.

(56) References Cited

U.S. PATENT DOCUMENTS

| | | | |
|---|---|---|---|
| 8,728,780 B2 | 5/2014 | Wada et al. | |
| 9,034,615 B2 | 5/2015 | Soucaille | |
| 2002/0164729 A1 | 11/2002 | Skraly et al. | |
| 2012/0178136 A1 | 7/2012 | Dischert et al. | |
| 2012/0315682 A1 | 12/2012 | Dischert et al. | |
| 2014/0295510 A1 | 10/2014 | Koivistoinen et al. | |

FOREIGN PATENT DOCUMENTS

| | | |
|---|---|---|
| EP | 2025760 A1 | 2/2009 |
| JP | S54119089 A | 9/1979 |
| JP | H10-174593 A | 6/1998 |
| JP | H10-174594 A | 6/1998 |
| WO | 2007/141316 A2 | 12/2007 |
| WO | 2016/193540 A1 | 12/2016 |

OTHER PUBLICATIONS

Pellicer et al., Journal of Bacteriology 178(7):2051-2059, 1996.*
Sousa et al., Microbiology 148(Pt5):1291-1303, 2002.*
Witkowski et al., Biochemistry 38:11643-11650, 1999.*
Tang et al., Phil Trans R Soc B 368:20120318, 1-10, 2013.*
Seffemick et al., J. Bacteriol. 183(8):2405-2410, 2001.*
Branden et al., Introduction to Protein Structure, Garland Publishing Inc., New York, p. 247, 1991.*
Sadowski et al., Current Opinion in Structural Biology 19:357-362, 2009.*
Pereira et al., "Efficient utilization of pentoses for bioproduction of the renewable two-carbon compounds ethylene glycol and glycolate", Metabolic Engineering, 2016, vol. 34, pp. 80-87.
Alkim et al., "The synthetic xylulose-1 phosphate pathway increases production of glycolic acid from xylose-rich sugar mixtures", Biotechnology for Biofuels, 2016, vol. 9, vol. 201, 11 pages.
Bar-Even et al., "Design and analysis of metabolic pathways supporting formatotrophic growth for electricity-dependent cultivation of microbes", Biochimica et Biophysica Acta, 2013, vol. 1827, pp. 1039-1047.
Boronat et al., "Experimental evolution of a metabolic pathway for ethylene glycol utilization by *Escherichia coli*", Journal of Bacteriology, 1983, vol. 153, No. 1, pp. 134-139.
Brouns et al., "Identification of the Missing Links in Prokaryotic Pentose Oxidation Pathways", The Journal of Biological Chemistry, 2006, vol. 281, No. 37, pp. 27378-27388.
Cam et al., "Engineering of a Synthetic Metabolic Pathway for the Assimilation of (d)-Xylose into Value-Added Chemicals", ACS Synth. Biol., 2016, vol. 5, pp. 607-618.

(Continued)

*Primary Examiner* — Delia M Ramirez
(74) *Attorney, Agent, or Firm* — MH2 Technology Law Group, LLP

(57) ABSTRACT

Processes, systems and microorganisms are described herein for producing glycolate from ethylene glycol. The processes generally comprise supplying a fermentation broth into a fermentation vessel, wherein the fermentation broth comprises ethylene glycol and a microorganism having a functional metabolic pathway for utilizing ethylene glycol as a carbon source. In a growth phase, an oxygen-containing gas is injected into the fermentation broth to provide oxygen bio-availability conditions to promote cell growth of the microorganism and limit accumulation of glycolate in the fermentation broth. In a production phase, an oxygen-containing gas is injected into the fermentation broth to provide oxygen bio-availability conditions to promote production of glycolate from ethylene glycol by the microorganism and accumulation of the glycolate in the fermentation broth, to produce a glycolate enriched broth.

12 Claims, 9 Drawing Sheets

Specification includes a Sequence Listing.

(56) References Cited

OTHER PUBLICATIONS

Child et al., "Microbial metabolism of aliphatic glycols bacterial metabolism of ethylene glycol", Biochimica et Biophysica Acta, 1978, vol. 538, pp. 316-327.

Deng et al., "Metabolic engineering of *E. coli* for efficient production of glycolic acid from glucose", Biochemical Engineering Journal, 2015, vol. 103, pp. 256-262.

Erickson et al., "Perspective on opportunities in industrial biotechnology in renewable chemicals", Biotechnology Journal, 2012, vol. 7, pp. 176-185.

Gao et al., "Enhanced Bioconversion of Ethylene Glycol to Glycolic Acid by a Newly Isolated *Burkholderia* sp. EG13", Appl. Biochem. Biotechnol., 2014, vol. 174, pp. 1572-1580.

Gaston et al., "Fermentation of ethylene glycol by *Clostridium glycolicum*, sp. N", J Bacteriol., 1963, vol. 85, pp. 356-362.

Gibson et al., "Enzymatic assembly of DNA molecules up to several hundred kilobases", Nature Methods, May 2009, vol. 6, No. 5, pp. 343-345.

Hartmanis et al., "Diol metabolism and diol dehydratase in Clostridium glycolicum", Archives of Biochemistry and Biophysics, Feb. 1986, vol. 245, No. 1, pp. 144-152.

Isobe et al., "A new enzymatic method for glycolaldehyde production from ethylene glycol", Journal of Molecular Catalysis B: Enzymatic., 1995, vol. 1, No. 1, pp. 37-43.

Isobe, "Oxidation of Ethylene Glycol and Glycolic Acid by Glycerol Oxidase", Bioscience, Biotechnology, and Biochemistry, 1995, vol. 59, No. 4, pp. 576-581.

Jiang et al., "Turning carbon dioxide into fuel", Philos. Trans. A. Math. Phys. Eng. Sci., 2010, vol. 368, pp. 3343-3364.

Kataoka et al., "Glycolic Acid Production Using Ethylene Glycol-Oxidizing Microorganisms", Biosci. Biotechnol. Biochem., 2001, vol. 65, No. 10, pp. 2265-2270.

Kishi et al., "Heterotrophic utilization of ethylene glycol and propylene glycol by Chlorella protothecoides", Algal Research, 2015, vol. 11, pp. 428-434.

Klein et al., "A novel dye-linked formaldehyde dehydrogenase with some properties indicating the presence of a protein-bound redox-active quinone cofactor", Biochem. J., 1994, vol. 301, pp. 289-295.

Koivistoinen et al.,"Glycolic acid production in the engineered yeasts *Saccharomyces cerevisiae* and Kluyveromyces actis", Microbial Cell Factories, 2013, vol. 12, No. 82, 16 pages.

Kortlever et al., "Catalystsand Reaction Pathways for the Electrochemical Reduction of Carbon Dioxide", J. Phys. Chem. Lett., 2015, vol. 6, pp. 4073-4082.

Kuhl et al., "New insights into the electrochemical reduction of carbon dioxide on metallic copper surfaces", Energy Environ. Sci., 2012,vol. 5, pp. 7050-7059.

Levin et al., "The ternary complex of Pseudomonas aeruginosa alcohol dehydrogenase with NADH and ethylene glycol", Protein Science, 2004, vol. 13, No. 6, pp. 1547-1556.

Liao et al. "Fuelling the future: microbial engineering for the production of sustainable biofuels", Nature Reviews Microbiology, 2016, vol. 14, No. 5, pp. 288-304.

Lu et al.,"Evolution of an *Escherichia coli* Protein with Increased Resistance to Oxidative Stress*", The Journal of Biological Chemistry, Apr. 1998, vol. 273, No. 14, pp. 8308-8316.

Malik et al., "Electrochemical reduction of CO2 for synthesis of green fuel", WIREs Energy Environ, 2017, e244, doi:10.1002/wene.244, 17 pages.

Muckschel et al., "Ethylene Glycol Metabolism by Pseudomonas putida", Applied and Environmental Microbiology, Dec. 2012, vol. 78, No. 24, pp. 8531-8539.

Pandit et al., "Redesigning metabolism based on orthogonality principles", Nature Communications, 2017, vol. 8, No. 15188, 11 pages.

Peterson et al., "How copper catalyzes the electroreduction of carbon dioxide into hydrocarbon fuels", Energy & Environmental Science, 2010, vol. 3, pp. 1311-1315.

Pirkov et al., "Ethylene production by metabolic engineering of the yeast *Saccharomyces cerevisiae*", Metabolic Engineering, 2008, vol. 10, pp. 276-280.

Shen et al., "Synergy as design principle for metabolic engineering of 1-propanol production in *Escherichia coli*", Metabolic Engineering, 2013, vol. 17, pp. 12-22.

Siegel et al. "Computational protein design enables a novel one-carbon assimilation pathway", PNAS, 2015, vol. 112, No. 12, pp. 3704-3709.

Smanski et al., "Functional optimization of gene clusters by combinatorial design and assembly", Nature Biotechnology, Dec. 2014, vol. 32, No. 12, pp. 1241-1249.

Straub et al., "Selective enhancement of autotrophic acetate production with genetically modified Acetobacterium woodii". Journal of Biotechnology, 2014, vol. 178, pp. 67-72.

Tamura et al., "Electrochemical reduction of CO2 to ethylene glycol on imidazolium ion-terminated self-assembly monolayer-modified Au electrodes in an aqueous solution", Phys. Chem. Chem. Phys., 2015, vol. 17, pp. 26072-26078.

Toraya et al., "Fermentation of 1,2-propanediol with 1,2-ethanediol by some genera of Enterobacteriaceae, involving coenzyme B12-dependentdiol dehydratase", Journal of Bacteriology, Jul. 1979, vol. 139, No. 1, pp. 39-47.

Wei et al., "High cell density fermentation of Gluconobacter oxydans DSM 2003 for glycolic acid production", J. Ind. Microbiol. Biotechnol., 2009, vol. 36, pp. 1029-1034.

Yang et al., "Electrochemistry of Carbon Dioxide on Carbon Electrodes", ACS Appl. Mater. Interfaces, 2016, vol. 8, pp. 28357-28371.

Zahoor et al., Metabolic engineering of Corynebacterium glutamicum for glycolate production, Journal of Biotechnology, 2014, vol. 192, pp. 366-375.

Zhang et al., "Enhancement of cell growth and glycolic acid production by overexpression of membrane-bound alcohol dehydrogenase in Gluconobacter oxydans DSM 2003", Journal of Biotechnology, 2016, vol. 237, No. 10, pp. 18-24.

Zhang et al., "Oxidation of ethylene glycol to glycolaldehyde using a highly selective alcohol dehydrogenase from Gluconobacter oxydans", Journal of Molecular Catalysis B: Enzymatic, 2015, vol. 112, pp. 69-75.

International Search Report and Written Opinion dated Dec. 11, 2018 for International Application No. PCT/CA2018/051081 (Authorized officer, Stephen Mahoney),14 pages.

\* cited by examiner

SEQUENCE LISTING

```
<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: aldA primer

<400> SEQUENCE: 1
aacaaaatga ggaggtactg ag                                              22

<210> SEQ ID NO 2
<211> LENGTH: 16
<212> TYPE: DNA
<213> ORGANISM: Artificial Sequence
<220> FEATURE:
<223> OTHER INFORMATION: fucO primer

<400> SEQUENCE: 2
aagttaagag gcaaga                                                     16
```

PRODUCTION OF GLYCOLATE FROM ETHYLENE GLYCOL AND RELATED MICROBIAL ENGINEERING

CROSS-REFERENCE TO RELATED APPLICATIONS

This application is a U.S. National Stage application of PCT/CA2018/051081 filed 6 Sep. 2018, which claims priority to U.S. Provisional Patent Application No. 62/555,431 filed 7 Sep. 2017, and U.S. Provisional Patent Application No. 62/597,510 filed 12 Dec. 2017, the entire disclosures of which are incorporated herein by reference.

SEQUENCE LISTING

The instant application contains a Sequence Listing which has been submitted electronically in ASCII format and is hereby incorporated by reference in its entirety. Said ASCII copy, created on 8 Mar. 2020, is named 2018-09-26_Sequence_Listing_17978-32_ST25.txt and is 1 Kilobytes in size.

TECHNICAL FIELD

The technical field generally relates to the production of glycolate from ethylene glycol, particularly using certain microorganisms as well as cultivation conditions and processing techniques.

BACKGROUND

Glycolic acid is an alpha-hydroxy acid used in the manufacture of biodegradable polymers such as polyglycolic acid (PGA), polylactic-glycolic acid (PLGA) and other degradable polymers, as well as being used as an ingredient in a number of industrial and household products such as solvents, paints, and especially cosmetics. Today, commercial production of glycolic acid is largely produced through the use of petrochemical feedstocks and by using highly toxic starting materials such as formaldehyde. Hence, it is desirous to produce this important chemical from a non-toxic, renewable source.

In contrast, some chemicals can be produced electrochemically. Ethylene glycol is one such chemical that is also a promising feedstock for bioprocesses because it can be derived from $CO_2$ and for which a process has been developed (Tamura et al. 2015). In this regard, its utilization as a feedstock for biological processes is important because it can serve as a replacement for glucose in modern bioprocesses such as those produced from point source emissions.

Some other bioprocesses also exist for producing glycolic acid. These conventional approaches to glycolic acid by genetically modified microorganisms have instead focused on using sugars as the substrate for production. Several studies have been published that have examined glycolic acid production from glucose and xylose (Deng et al. 2015; Alkim et al. 2016; Koivistoinen et al. 2013; Zahoor et al. 2014; Cam et al. 2016). The highest of these reports achieves titers of 56.44 g/L and a yield of 0.52 g/g. However, the use of sugar feedstocks presents limitations such as it does not allow the capture of point source carbon emissions.

Thus, a possible advantage of embodiments disclosed herein can be to provide a biological method for glycolate production that uses a carbon feedstock that can be derived renewably and does not utilize toxic compounds such as formaldehyde. Secondly, whereas previously developed biological methods for producing glycolate have been described in the literature, large-scale production of glycolate using those methods have certain drawbacks. For example, the production of glycolic acid from ethylene glycol by biological methods has relied on the use of a co-substrate to provide cell growth or to induce expression of the ethylene glycol metabolizing enzymes. The use of co-substrates can present certain challenges for large-scale glycolate production over the use of a single substrate, such as additional cost. Moreover, other biological methods for producing glycolic acid have been performed under neutral pH conditions. Whereas the production of glycolic acid lowers the pH of the fermentation broth, it would be preferable to have a culturing environment less than pH 7.2 such that the costs of glycolic acid production can be decreased as less buffer is required for the media to maintain a neutral pH.

For example, the biological production of glycolic acid has been described by various authors. However, previous methods have a number of drawbacks. Previous knowledge on the conversion of ethylene glycol to glycolic acid by a natural or genetically modified microorganism has relied on the oxidation of ethylene glycol in a phosphate buffered medium or in distilled water and has relied on a resting cell biotransformation for the accumulation of glycolic acid. This has certain disadvantages, such as requiring the separation of biomass from the culturing media followed by resuspension of that biomass into fresh media for resting cell transformation at much larger cell densities. Thus, a disadvantage of such processes is the need for additional equipment like a secondary vessel to carry out biotransformation or additional centrifuges for cell separation and concentration.

In addition, several previous methods rely on using ethylene glycol as a secondary carbon source for biotransformation, in addition to a primary carbon source for growth such as glucose, sorbitol or even propylene glycol. The reliance on a secondary carbon source for growth can be an additional cost for the process.

A disadvantage of other previous methods for producing glycolic acid employing genetically modified microorganisms is that they employ oxygen sensitive enzymes. The production of glycolic acid requires oxygen as a substrate. However, under high oxygen concentrations or mass transfer rates such as those that might be expected in an industrial bioreactor, it is necessary that the microorganism remain viable by having functional enzymes. Hence, the use of oxygen sensitive enzymes for producing glycolic acid can have a detrimental effect on the productivity and titres of the process.

In several alternative known methods, glycolic acid production occurs at a pH near or above 7. When organic acids are produced during a fermentation, the result is a drop in pH of the fermentation broth. Hence, it is more economically viable to operate the fermentation at a lower pH since it requires the addition of less base or buffer to the fermentation medium. Therefore, a disadvantage of several alternatives is that they operate at a pH near to or greater than neutral.

Thus, there is a need for technologies that overcome or mitigate at least some of the disadvantages of known methods.

SUMMARY

Various aspects, implementations, embodiments and features of the invention are described herein.

In some implementations, the invention relates to the development of a microorganism and the cultivation conditions for the microorganisms to grow on ethylene glycol and produce glycolic acid. In some implementations, the invention relates to methods of producing glycolic acid from a substrate substantially comprising ethylene glycol using a microorganism, which may have been previously genetically engineered to have certain characteristics, and using certain process operating conditions.

Described herein are methods for producing glycolic acid, by culturing genetically modified microorganisms in the presence of ethylene glycol as the sole carbon source for growth and for glycolate production. In a preferred embodiment, air is introduced into the fermentation vessel such that the oxygen uptake rate (OUR) is greater than about 6 mmol/gDW/h to promote cellular respiration and then a second set of culturing conditions is established wherein the oxygen uptake rate is lowered to below about 6 mmol/gDW/h such that glycolic acid accumulated in the fermentation medium at a concentration greater than 1 g/L but in a preferred embodiment greater than 10 g/L.

In some embodiments, the culturing media occurs at a pH less than 7.2 but in a preferred embodiment where the pH is less than about 6.5 (during the production phase).

In some embodiments, the genetically modified microorganism comprises a functional metabolic pathway for converting ethylene glycol to pyruvate, wherein that metabolic pathway comprises an alcohol dehydrogenase that is tolerant to oxygen with enhanced activity that converts ethylene glycol to glycolaldehyde and an aldehyde reductase with enhanced activity that converts glycolaldehyde to glycolic acid.

In some embodiments, the method for producing glycolic acid from ethylene glycol comprises an active and functional endogenous glycolate oxidase whose activity may be dynamically controlled through the use of a combination of mechanisms that affect the gene promoter, gene inactivation by protein degradation and/or gene inactivation by allosteric control.

In some aspects of the method for the production glycolic acid, the concentration of genetically modified microorganisms in the fermenter in dry mass is less than about 10 g/L.

In some embodiments, the glycolic acid obtained during the production phase is greater than 50% yield by mass on ethylene glycol but preferably greater than 80%.

In some embodiments of the method for producing glycolic acid, the fermentation can be separated into two distinct phases dominated by a primary growth phase where there is little glycolic acid production and a second phase dominated glycolic acid production and there is little biomass production.

In some implementations, the present invention allows for the production of glycolic acid without the use of a secondary carbon source such as glucose since ethylene glycol serves as both a growth substrate as well as the precursor for producing glycolic acid. This has significant commercial benefits because it allows the fermentation to occur in a single vessel, without the need to separate the genetically modified microorganisms from its growth media. This simplification allows production of glycolic acid to require fewer fermentation and biotransformation vessels which would reduce the capital costs of the process.

In some implementations, the present invention utilizes an oxygen tolerant version of an alcohol dehydrogenase to catalyze the first step of the metabolic pathway for converting ethylene glycol to glycolic acid.

In some implementations, the present invention employs a two-stage fermentation method wherein genetically modified microorganisms are cultured at a neutral pH but wherein the glycolate production phase occurs at a pH less than 7, preferably about 6.5.

In some implementations, the present invention includes a method for producing glycolic acid by culturing a genetically modified organism such as *E. coli* cells in the presence of ethylene glycol.

In another implementation, there is provided a process for producing glycolate from ethylene glycol, comprising: supplying a fermentation broth into a fermentation vessel, wherein the fermentation broth comprises ethylene glycol and a microorganism genetically engineered for increased conversion of ethylene glycol to glycolaldehyde (and eventually glycolate) in the presence of oxygen as compared to a corresponding microorganism lacking the genetic engineering, the genetically engineered microorganism being responsive to a decrease in oxygen bio-availability to transition from a cell growth promoting metabolic pathway in which conversion of glycolate to glyoxylate is promoted to a glycolate production metabolic pathway in which the conversion of glycolate to glyoxylate is inhibited; in a growth phase, injecting an oxygen-containing gas into the fermentation broth and providing initial oxygen bio-availability conditions to utilize the cell growth promoting metabolic pathway to promote cell growth of the microorganism and limit accumulation of glycolate in the fermentation broth; in a production phase, injecting an oxygen-containing gas into the fermentation broth and providing reduced oxygen bio-availability conditions to utilize the glycolate production metabolic pathway to promote production of glycolate from ethylene glycol by the microorganism and accumulation of the glycolate in the fermentation broth, to produce a glycolate enriched broth; and recovering at least a portion of the glycolate from the glycolate enriched broth.

In some implementations, there is provided a process for producing glycolate, comprising: supplying a fermentation broth into a fermentation vessel, wherein the fermentation broth comprises ethylene glycol and a microorganism having a functional metabolic pathway for utilizing ethylene glycol as a carbon source; in a growth phase, injecting an oxygen-containing gas into the fermentation broth and providing oxygen bio-availability conditions to promote cell growth of the microorganism and limit accumulation of glycolate in the fermentation broth; and in a production phase, injecting an oxygen-containing gas into the fermentation broth and providing oxygen bio-availability conditions to promote production of glycolate from ethylene glycol by the microorganism and accumulation of the glycolate in the fermentation broth, to produce a glycolate enriched broth.

In some implementations, the microorganism has a functional metabolic pathway for converting ethylene glycol to pyruvate. The functional metabolic pathway can include polypeptides catalyzing reactions: (a) ethylene glycol to glycolaldehyde; (b) glycolaldehyde to glycolate; and (c) glycolate to glyoxylate. One or more of the polypeptides can be encoded by one or more polynucleotides that are exogenous and/or heterologous with respect to the microorganism. Expression of one or more of the polynucleotides can be under control of one or more regulatory elements. One or more of the regulatory elements can enable control of expression of one or more of the polynucleotides in response to oxygen levels, pH, nutrient concentrations such as phosphate or nitrogen, the presence or concentration of an inducer, and/or another parameter controllable during fermentation. One or more of the regulatory elements can include one or more promoters and/or terminators operably linked to the one or more polynucleotides. One or more of the regulatory elements can be exogenous and/or heterologous with respect to the microorganism. One or more of the polynucleotides can be comprised in a plasmid. One or more of the polynucleotides can be integrated into the genome of the microorganism.

In some implementations, the polypeptide catalyzing reaction (a) comprises an enzyme of class E.C. 1.1.1, E.C. 1.1.3, or E.C. 1.1.5, or a functional variant or fragment thereof, which converts ethylene glycol to glycolaldehyde. The functional variant can be a variant having reduced sensitivity to oxygen. The reduced sensitivity to oxygen can include reduced sensitivity to metal catalyzed oxidation. The polypeptide catalyzing reaction (a) can include lactaldehyde reductase. The lactaldehyde reductase can be encoded by the gene fucO. The lactaldehyde reductase can include an amino acid substitution I7L and/or L8V or L8M, based on the amino acid numbering of the native lactaldehyde reductase encoded by fucO from *E. coli* MG1655.

In some implementations, the polypeptide catalyzing reaction (a) comprises an enzyme that uses an oxygen-insensitive cofactor. The enzyme can use a cofactor other than iron, which can be zinc (e.g., a zinc-dependent alcohol dehydrogenase or an NAD-dependent alcohol dehydrogenase).

In some implementations, the polypeptide catalyzing reaction (b) comprises an enzyme of class E.C. 1.2.1, E.C. 1.2.3, or E.C. 1.2.5, or a functional variant or fragment thereof which converts glycolaldehyde to glycolate. The polypeptide catalyzing reaction (b) can include lactaldehyde dehydrogenase. The lactaldehyde dehydrogenase can be encoded by the gene aldA.

In some implementations, the polypeptide catalyzing reaction (c) can include an enzyme of class E.C. 1.1.3.15, or a functional variant or fragment thereof, which converts glycolate to glyoxylate. In some implementations, the polypeptide catalyzing reaction (c) comprises glycolate oxidase.

In some implementations, the microorganism further comprises a polynucleotide encoding a polypeptide catalyzing reaction (d) export of intracellular glycolate to the extracellular environment. The polypeptide catalyzing reaction (d) can be exogenous and/or heterologous with respect to the microorganism.

In some implementations, the microorganism comprises a polynucleotide encoding a polypeptide that catalyzes both reactions (a) and (b).

In some implementations, the microorganism further comprises one or polynucleotides encoding one or more enzymes for converting glycolate to polyglycolic acid, ethanolamine, or glycine. The microorganism further can include an exporter of polyglycolic acid, ethanolamine, or glycine that exports intracellular polyglycolic acid, ethanolamine, or glycine to the extracellular environment.

In some implementations, the microorganism is bacteria (e.g., *Escherichia coli*) which can be genetically modified for improved tolerance to acidic pH, as compared to corresponding wild-type bacteria.

In some implementations, the microorganism is a yeast or fungus; or a yeast or a fungus that is genetically modified for improved tolerance to acidic pH, as compared to a corresponding wild-type yeast or fungus.

The yeast or fungus can be from the species *Candida boidinii, Candida etchellsii, Candida geochares, Candida lambica, Candida sorbophila, Candida sorbosivorans, Candida sorboxylosa, Candida vanderwaltii, Candida zemplinina, Debaryomyces castellii, Issatchenkia orientalis, Kluyveromyces lactis, Kluyveromyces marxianus, Pichia anomala, Pichia jadinii, Pichia jadinii, Pichia membranifaciens, Saccharomyces bayanus, Saccharomyces bulderi, Saccharomycopsis crataegensis, Zygosaccharomyces bisporus, Zygosaccharomyces kombuchaensis*, or *Zygosaccharomyces lentus*.

In some implementations, the microorganism is from *Pseudomonas* species, *Clostridium* species, *Chlorella* species or other algae, *Gluconobacter oxydans, Pichia naganishii, Corynebacterium* species, or *Corynebacterium glutamicum*; or from a microorganism thereof that is genetically modified for improved tolerance to acidic pH, as compared to a corresponding wild-type microorganism.

In some implementations, the microorganism is from *Haloferax mediterranei, Halobactreium salinarum, Nicotiana tabacum*, or *Thermus thermophilus*; or from a microorganism thereof that is genetically modified for improved tolerance to acidic pH, as compared to a corresponding wild-type microorganism.

The microorganism can be for use in the fermentative production of glycolate, polyglycolic acid, ethanolamine, and/or glycine. In some implementations, there is provided a use of the microorganism as defined above or herein for the fermentative production of glycolate, polyglycolic acid, ethanolamine, and/or glycine.

In some implementations of processes described herein, the main carbon source for the microorganism is the ethylene glycol. In addition, the only carbon source for the microorganism can be the ethylene glycol.

In some implementations of processes described herein, the microorganism is genetically engineered for increased conversion of ethylene glycol to glycolaldehyde (and eventually glycolate) in the presence of oxygen as compared to a corresponding microorganism lacking the genetic engineering, and is responsive to a decrease in oxygen bioavailability to transition from a cell growth promoting metabolic pathway in which conversion of glycolate to glyoxylate is promoted to a glycolate production metabolic pathway in which the conversion of glycolate to glyoxylate is inhibited.

In some implementations, the process includes recovering at least a portion of the glycolate from the glycolate enriched broth. The recovering can include removing the glycolate enriched broth from the fermentation vessel, separating cells from the glycolate enriched broth to produce a biomass-depleted broth, and producing a glycolate enriched stream from the biomass-depleted broth.

In some implementations, the process includes recycling or reusing at least a portion of the cells separated from the glycolate enriched broth back into the fermentation vessel. In some implementations, the process includes releasing a liquid portion of the glycolate enriched broth from the fermentation vessel, and producing a glycolate enriched stream from the liquid portion. In some implementations, the process includes retaining cells within the fermentation vessel, replenishing the fermentation vessel with additional broth and ethylene glycol, and reusing the retained cells for additional production of glycolate.

In some implementations, the glycolate production is conducted as a batch or fed-batch process.

In some implementations, the fermenter vessel has a chamber in which the fermentation broth is located and in which the microorganism cell growth and glycolate production both occur. In some implementations, there is no additional step to carry out biotransformation after fermentation. The oxygen-containing gas can include or be air. In some implementations, the oxygen-containing gas is introduced during the growth phase at a sufficiently elevated concentration to inhibit extracellular accumulation of glycolate in the fermentation broth. The oxygen-containing gas can be introduced during the production phase at a sufficiently low concentration to inhibit metabolic conversion of glycolate into a corresponding metabolite. The oxygen-containing gas can be introduced during the growth phase above an oxygen bio-availability minimum threshold, and during the production phase below an oxygen bio-availability maximum threshold.

In some implementations, the oxygen bio-availability minimum threshold and the oxygen bio-availability maximum threshold are predetermined. The oxygen bio-availability minimum threshold and the oxygen bio-availability maximum threshold can be the same value. The oxygen bio-availability minimum threshold can be between 4 mmol/gDW/h and 8 mmol/gDW/h. The oxygen bio-availability maximum threshold can be between 4 mmol/gDW/h and 8 mmol/gDW/h and can be below the oxygen bio-availability minimum threshold. The oxygen bio-availability maximum threshold can be greater than about 6 mmol/gDW/h, and the oxygen bio-availability minimum threshold can be below about 6 mmol/gDW/h; and/or the oxygen bio-availability maximum and minimum thresholds can be different from each other by at least 0.5 mmol/gDW/h, by at least 1 mmol/gDW/h, by at least 2 mmol/gDW/h, by at least 3 mmol/gDW/h, by at least 4 mmol/gDW/h, and/or by at most 4 mmol/gDW/h.

In some implementations, the production phase is operated and controlled such that a concentration of extracellular glycolate in the fermentation broth is greater than about 1 g/L, optionally greater than 2 g/L, 5 g/L, 7 g/L, 10 g/L or 15 g/L, prior to removal of the glycolate from the fermentation broth. In some implementations, the growth phase is conducted at a pH of about 7, optionally at a pH of about 6.5 to about 7.2, still further optionally at a pH of less than 7.2.

In some implementations, the production phase is conducted at a pH of less than 7, optionally at a pH of less than 6.5, and still further optionally at a pH of about 6 to about 6.9. In some implementations, the growth phase is conducted at a temperature greater than 30° C., optionally between 30° C. and 42° C., between 33° C. and 40° C., between 36° C. and 38° C., or at about 37° C.

In some implementations, the production phase is conducted at a temperature greater than 30° C., optionally between 30° C. and 42° C., between 33° C. and 40° C., between 36° C. and 38° C., or at about 37° C.; or still further optionally at a temperature that is generally the same as that of the growth phase. In some implementations, the growth phase is conducted at an air injection rate that is determined based on design of the fermentation vessel and the desired oxygen bio-availability minimum threshold.

In some implementations, the production phase is conducted at an air injection rate that is determined based on design of the fermentation vessel and the desired oxygen bio-availability maximum threshold.

In some implementations, the growth phase is conducted at a pH of about 7 and/or a temperature of about 37° C. The production phase can be conducted at a pH of about 6.5 and/or at a pH that is about 0.5 lower than that of the growth phase, and/or a temperature of about 37° C. and/or a temperature generally the same as that of the growth phase.

In another implementation, there is provided a process for producing glycolate, comprising: providing a fermentation broth comprising a carbon source and a microorganism, wherein the ethylene glycol is a primary component of the carbon source; and providing fermentation conditions to induce conversion the ethylene glycol into glycolate by the microorganism, and accumulation of the glycolate in the fermentation broth. In such an implementation, the process can include one or more features from any one of the previous paragraphs or items described herein.

In another implementation, there is provided a process for producing glycolate by microbial conversion of ethylene glycol into glycolate using a microorganism that is genetically engineered to consume ethylene glycol and comprises a polynucleotide encoding a lactaldehyde reductase and/or a polynucleotide encoding a lactaldehyde dehydrogenase.

In another implementation, there is provided a process for producing glycolate by microbial conversion of ethylene glycol into glycolate using a microorganism that is genetically engineered for increased conversion of ethylene glycol into a first corresponding metabolite in the presence of oxygen as compared to a corresponding microorganism lacking the genetic engineering, and for oxygen-dependent conversion of glycolate into a second corresponding metabolite.

In such process implementations, the process can include one or more features from any one of the previous paragraphs or items described herein.

Further background and details regarding optional embodiments, aspects, experiments and examples related to the invention are described below.

DETAILED DESCRIPTION

Ethylene glycol can be used as a substrate for microbial conversion into glycolate, where the production process can leverage certain features of the microorganism and process operating conditions to enhance performance.

For instance, the process can be controlled such that oxygen availability and uptake by the microorganism are varied over time to facilitate a two-phase process, the first phase being a growth phase promoting cell growth and limiting glycolate accumulation and the second phase being a glycolate production phase promoting glycolate accumulation in a fermentation broth. This two-phase process can be facilitated by controlling oxygen uptake conditions in the fermentation broth, e.g., by varying air injection rates, such that the growth phase has high oxygen uptake rates and the production phase has lower oxygen uptake rates.

In addition, the microorganism that is deployed in the process can be a genetically engineered microorganism that has features enabling improved performance for glycolate production from ethylene glycol. For instance, the microorganism can be engineered to comprise a functional metabolic pathway for converting ethylene glycol to pyruvate, wherein the metabolic pathway comprises the conversion of ethylene glycol to glycolaldehyde, and the conversion of glycolaldehyde to glycolate. Various microorganisms, such as bacteria or yeast, can be engineered pursuant to the methods described herein to provide an advantageous microorganism for glycolate production.

Furthermore, the process can include ethylene glycol as essentially the only carbon substrate for microbial growth and glycolate production. In such cases, trace amounts of other carbon sources can be present, but ethylene glycol is the dominant carbon source with no substantial co-substrates, such as glucose and/or xylose. For instance, the ethylene glycol can be at least 80 wt %, 85 wt %, 90 wt %, 95 wt %, or 99 wt % or 100 wt % of the carbon source for cell growth and/or for glycolate production, for example during the growth phase and the production phase.

Figure 7:
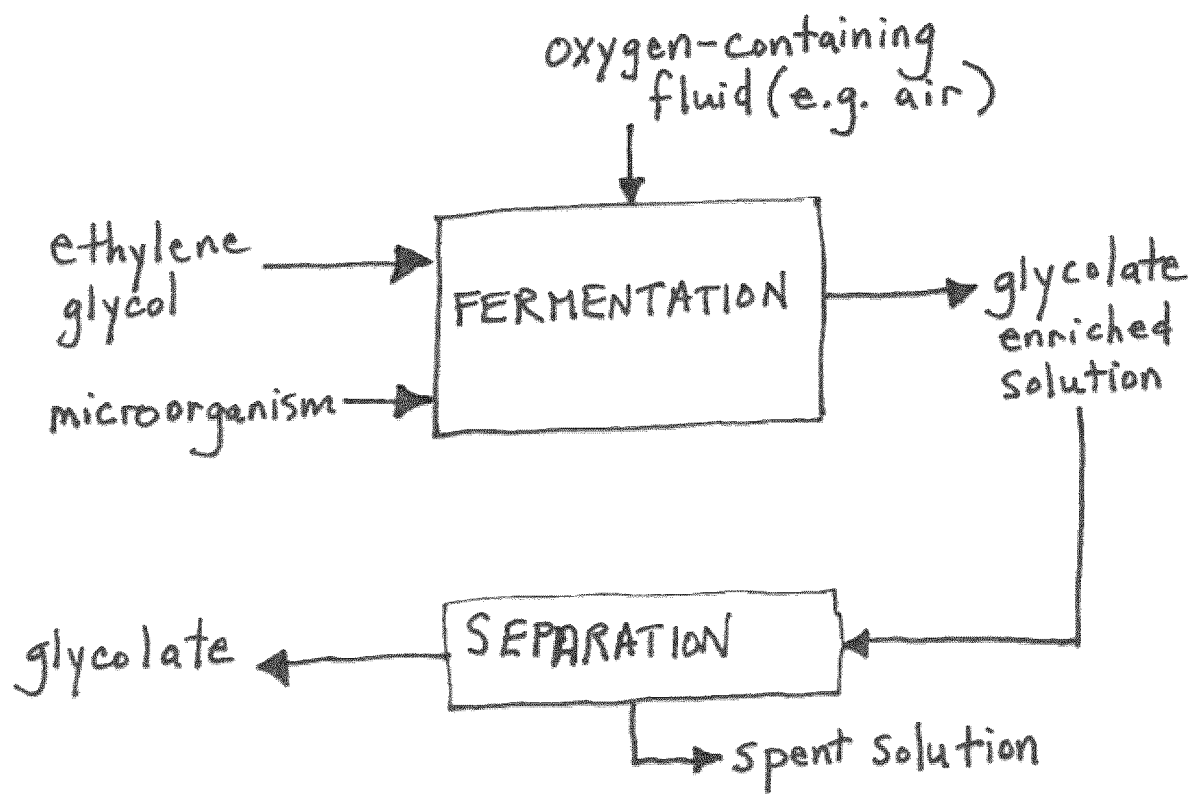
FIG. 7 is a block flow diagram for the production of glycolate from ethylene glycol.

Turning to FIG. 7, a general illustration of an example process is shown. Ethylene glycol and the microorganism are used in the fermentation step, along with an oxygen-containing fluid, such as an oxygen-containing gas like air. The fermentation can be a batch process, for example. At the end of the fermentation reaction, which can include the two-phase process control mentioned above, a glycolate enriched solution is produced and can be subjected to separation to produce glycolate (e.g., at higher concentrations or relatively pure) as well as a spent solution.

In terms of separating the glycolate from the fermentation broth, various methods can be used. For example, separation methods based on reactive extraction, crystallization, adsorption-elution, and so on, could be used. In some implementations, the fermentation broth including the biomass is removed from the fermentation vessel and is then subjected to a series of separation steps, e.g., biomass removal followed by glycolate extraction. Alternatively, a portion of the fermentation broth could be removed from the fermentation vessel while the biomass remains in the vessel, and then the biomass-depleted fermentation broth can be subjected to a separation technique to remove the glycolate. The unit operations can be designed and implemented depending on the process being batch, semi-batch or continuous.

It is also noted that the cells can be reused in a continuous process or a batch process. The cells could be separated from the glycolate rich fermentation broth, for example by centrifugation or other solid-liquid separation methods, and then reused in the fermentation vessel. In such a scenario, the process using recycled cells can be adapted such that the two-phase process may not be required as the cells may be ready for reuse in the production phase. Eventually the used cells can be removed from the process, for example after their viability period, after which a new cell culture can be introduced in the fermentation vessel and the two-phase process can be repeated. Thus, in some implementations, cells can be reused in the production phase through multiple batches, depending on viability and stability factors.

Figure 8:
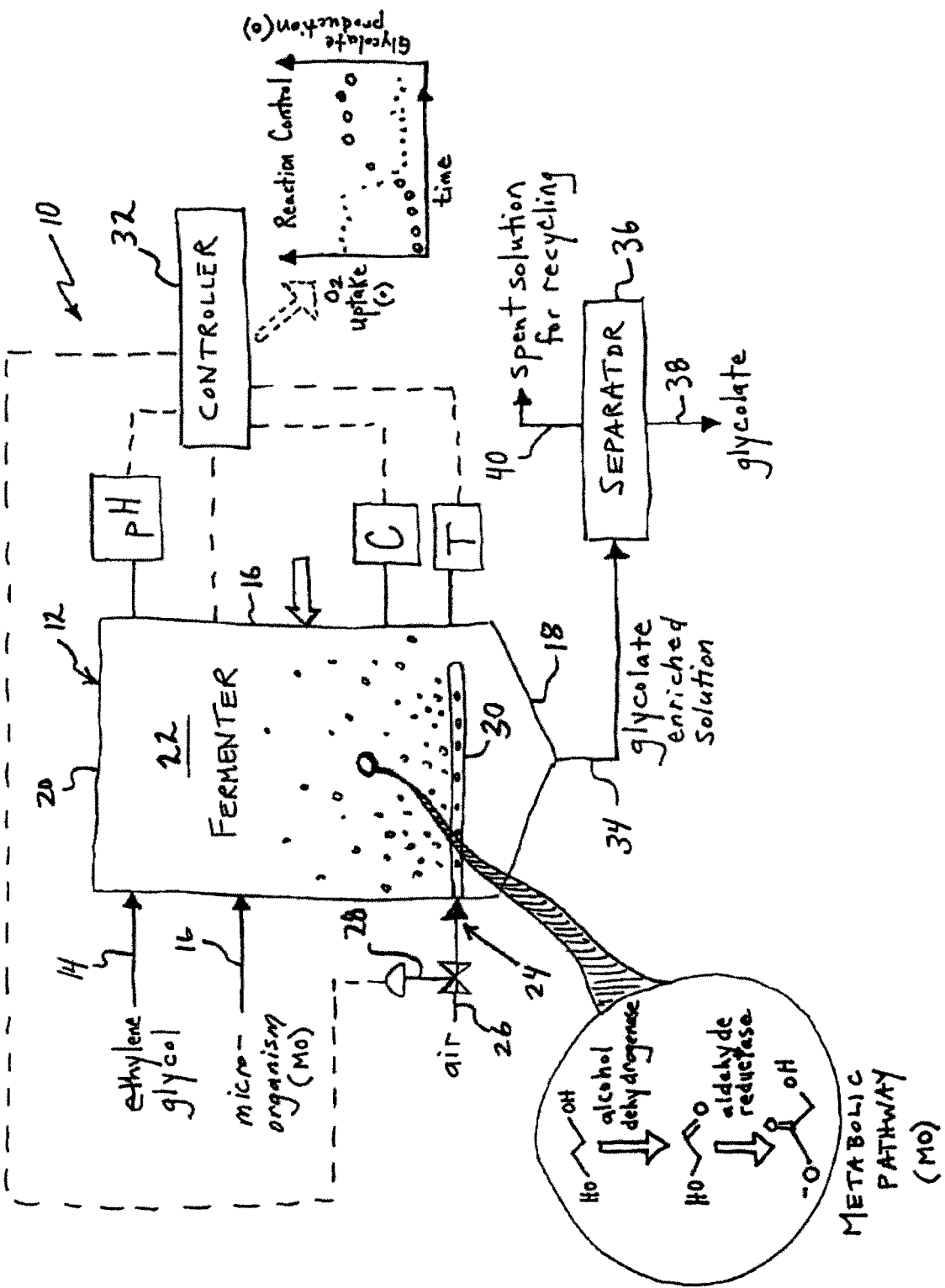
FIG. 8 is a schematic including a block flow diagram, an illustrative graph of two stage process control, and an illustration of the metabolic pathway for conversion of ethylene glycol to glycolate.

Referring to FIG. 8, a glycolate production system 10 can include a fermenter 12 to which a feed line 14 is coupled for feeding the ethylene glycol. A microorganism inlet 16 can also be provided to supply the microorganism to the fermenter 12. The fermenter also has side walls 16, a bottom 18 and a top 20 defining a fermentation chamber 22 in which the fermentation reactions occur. The feed materials form a fermentation broth within the fermentation chamber 22. An oxygen-containing fluid inlet 24 is also coupled to the fermenter 12 for feeding an oxygen-containing fluid into the fermentation broth. The oxygen-containing fluid can be air, for example, or another gas that includes oxygen. Multiple inlets for the various feed materials can also be provided. The oxygen-containing fluid inlet 24 can include a gas feed line 26 with a flow control device 28, such as a valve, to enable the flow rate of the gas to be controlled or adjusted. The oxygen-containing fluid inlet 24 can also include a sparging unit that has multiple outlet apertures distributed over the cross-section of the fermentation chamber 22 to inject gas bubbles into the fermentation broth.

FIG. 8 also shows that the system 10 can include various measurement devices coupled to the fermenter 12 to measure certain variables, such as temperature (T), pH, concentration (C), and so on. The system 10 can also include a controller 32 that can be coupled to various measurement devices to receive information, and also to control units of the fermenter 12 in order to modify one or more process operating conditions. For instance, the controller 32 can be configured to receive information regarding the cell growth progression of the microorganism in the fermentation broth, and to reduce the injection rate of the air by closing the valve 28 once the cell growth has sufficiently progressed, thereby initiating the second phase of the process. The controller 32 can also be configured to regulate the temperature by varying heat that is provided to the system, to regulate the pH by addition of a pH modifier to keep the pH within a desired window, and/or to initiate different phases of the process including the growth phase, the production phase, and then the recovery phase once a desired concentration of glycolate has been produced.

Various methods and variables can be used to monitor cell growth progression. For example, $CO_2$ off gas could be measured to determine growth progression. The monitoring is preferably based on measuring cell quantity, although other variables could be measured. Characteristics of the fermentation broth could be measured to infer cell growth progression. In addition, cell growth progression could be determined using various other techniques, or could be estimated based on previous experiments or operations such that active determination is not conducted but is rather estimated based on variables such as fermentation time.

Furthermore, in terms of monitoring or determining the impact of oxygen on the system, methods can be used to assess the bio-availability of oxygen and can include the amount of oxygen in the fermentation vessel as well as the mass transfer of the oxygen from the gas phase to the liquid phase. In some embodiments, another gas (e.g., carbon dioxide) may be measured as a proxy for oxygen levels. Bio-availability of oxygen can be controlled by adjusting gas feed rate into the vessel, rate of mixing in the vessel, temperature in the vessel or other parameters that impact solubility and dissolved oxygen, and/or oxygen content in the gas fed into the vessel (e.g., by co-feeding pure oxygen and/or pure nitrogen with air via the same inlet or separate inlets to increase or decrease oxygen content in the feed gas), and so on. Oxygen bio-availability can be estimated and controlled within each process phase, and also in order to transition from one phase to the other.

Other operating parameters can also be monitored and manipulated during the process. For example, pH can be changed when transitioning from growth to production phase. In addition, agitation could be changed during this transition, as well as temperature. Such parameters can be changed in order to impact the bio-availability of oxygen and/or to have other beneficial impacts on the process phase of interest.

FIG. 8 illustrated a close-up view of some of the chemical reactions that occur, notably the metabolic conversion of ethylene glycol into glycolaldehyde via alcohol dehydrogenase, followed by the metabolic conversion of glycolaldehyde into glycolate via aldehyde reductase. More regarding certain aspects and features of the microorganisms that can be used in the process is described further below.

Referring still to FIG. 8, once the fermentation is complete, the glycolate enriched solution can be evacuated from the fermenter 12 via an outlet line 34 and supplied to a separator 36 or other downstream processing units to produce a glycol stream 38 and a spent solution 40. Various downstream separation units can be used to separate the glycolate, e.g., filtration or centrifugation to remove biomass/cells, and then reactive extraction, crystallization, chromatography, and so on, to remove glycolate.

Microorganisms

The production of glycolate from ethylene glycol can be facilitated by the use of a genetically engineered microorganism having certain characteristics. For example, a microorganism can be engineered to comprise a functional metabolic pathway for converting ethylene glycol to pyruvate, wherein the metabolic pathway comprises polypeptides catalyzing (a) the conversion of ethylene glycol to glycolaldehyde, (b) the conversion of glycolaldehyde to glycolate, and (c) the conversion of glycolate to glyoxylate. The metabolic pathway may further comprise native and/or exogenous enzymes enabling the conversion of glyoxylate to pyruvate.

In some implementations, the microorganism has the ability to utilize ethylene glycol as a sole or dominant carbon source. By dominant carbon source, it is meant that the microorganism utilizes ethylene glycol primarily over other carbon sources such as glucose and/or xylose to support growth and/or chemical production (e.g., glycolate, or downstream glycolate metabolization products). As used herein, the expressions "microorganism has the ability to utilize ethylene glycol as a sole carbon source", "microorganism can utilize ethylene glycol as a sole carbon source", and "microorganism uses ethylene glycol as a sole carbon source" are used interchangeably as referring to a property or characteristic of the microorganism itself, and not necessarily to the content of the fermentation broth in which the microorganism is being employed.

In some implementations, the microorganism described herein is genetically engineered to exhibit sustained growth on ethylene glycol as the sole or main carbon source. In some implementations, the genetically engineered microorganism may exhibit at least 2-fold, 3-fold, 4-fold, 5-fold, 6-fold or more growth over a corresponding wild-type (or non-genetically engineered) microorganism, for example as measured at 24 hours post-inoculation by optical density (O.D.) at 600 nm, and/or in a growth phase of a process described herein. In some implementations, the genetically engineered microorganism has the ability to increase its cell density (number of cells per unit volume) by a factor of 2, 3, 4, 5, or 6, as compared to a corresponding wild-type (or non-genetically engineered) microorganism, when cultured in the presence of ethylene glycol as the sole or main carbon source, such as after initial non-ethylene glycol carbon sources are depleted from the starting/inoculation culture medium, when cultured in a growth phase of a process described herein.

In some implementations, the microorganism may be bacteria (e.g., *Escherichia coli*), that may be further genetically modified for improved tolerance to acidic pH, as compared to corresponding wild-type bacteria.

In some implementations, the microorganism may be a yeast or fungus, such as from the species *Candida boidinii*, *Candida etchellsii*, *Candida geochares*, *Candida lambica*, *Candida sorbophila*, *Candida sorbosivorans*, *Candida sorboxylosa*, *Candida vanderwaltii*, *Candida zemplinina*, *Debaryomyces castellii*, *Issatchenkia orientalis*, *Kluyveromyces lactis*, *Kluyveromyces marxianus*, *Pichia anomala*, *Pichia jadinii*, *Pichia jadinii*, *Pichia membranifaciens*, *Saccharomyces bayanus*, *Saccharomyces bulderi*, *Saccharomycopsis crataegensis*, *Zygosaccharomyces bisporus*, *Zygosaccharomyces kombuchaensis*, or *Zygosaccharomyces lentus*. Such species have been shown to exhibit improved tolerance to low pH environments. In some implementations, the yeast or fungus may be further genetically modified for improved tolerance to acidic pH, as compared to corresponding wild-type bacteria.

In some implementations, the microorganism may be from a species that naturally consumes ethylene glycol. Such species include for example *Pseudomonas* species (e.g., *Pseudomonas putida*; Muckschel et al., 2012), *Clostridium* species (Gaston and Stadtman, 1963), *Chlorella* species or other algae (Kishi et al., 2015), *Gluconobacter oxydans* (Zhang et al., 2016), or *Pichia naganishii* (Kataoka et al., 2001). In some implementations, the microorganism from such a species may be further genetically modified for improved tolerance to acidic pH, as compared to corresponding wild-type bacteria.

In some implementations, for example wherein the microorganism is from a species that naturally consumes ethylene glycol, the microorganism may be genetically modified to disrupt endogenous metabolic pathways for ethylene glycol uptake and/or utilization. Alternatively, the microorganism's native metabolic pathways for ethylene glycol uptake and/or utilization may be diverted to produce glycolate. Microorganisms that natively consume ethylene glycol may utilize one of two types of metabolic pathways.

The first pathway of ethylene glycol uptake/degradation utilizes a diol-dehydratase resulting in the dehydration of ethylene glycol to acetaldehyde. Acetaldehyde is then activated to acetyl-CoA by an acetaldehyde dehydrogenase enzyme which provides the cell with the key precursor metabolite to support growth via the TCA cycle and gluconeogenic pathways. The production of one mole of acetyl-CoA from one mole of ethylene glycol concomitantly produces one NADH. This pathway is most commonly found in some *Clostridium* species and a few other anaerobic organisms owing to the oxygen sensitivity of the diol-dehydratase[25,27]. Accordingly, in some implementations, the microorganism may comprise one or more (exogenous) polynucleotides encoding enzymes (e.g., a diol-dehydratase) that converts ethylene glycol to acetaldehyde. The microorganism may comprise one or more (exogenous) polynucleotides encoding an enzyme (e.g., an acetaldehyde dehydrogenase) that converts acetaldehyde to acetyl-CoA.

The second pathway of ethylene glycol uptake/degradation utilizes a pathway wherein ethylene glycol is successively oxidized using nicotinamide cofactors and oxygen to produce glyoxylate. Glyoxylate which is a gluconeogenic carbon substrate, can then be used as the growth metabolite as it enters lower glycolysis at the 2-phosphoglycerate node as well as the TCA cycle via the glyoxylate shunt. Accordingly, in some implementations, the microorganism can be genetically modified to express one or more of (exogenous) enzymes of this second pathway. In some implementations, the microorganism may be genetically modified to express one or more (exogenous) polynucleotides encoding one or more enzymes that convert glyoxylate to glycolate (e.g., glyoxylate reductase; EC 1.1.1.26); and/or engineer the microorganism to disrupt or delete a native glycolate oxidase enzyme.

In some implementations, the microorganism may be from a *Corynebacterium* species (e.g. *Corynebacterium glutamicum*).

In some implementations, the microorganism may be from *Haloferax mediterranei*, *Halobactreium salinarum*, *Nicotiana tabacum*, or *Thermus thermophilus*. Such organisms have the ability to grow under extreme conditions, which may be advantageous under certain implementations.

Genetic Modifications

In some implementations, the one or more polypeptides catalyzing reactions (a), (b) or (c) may be encoded by one or more polynucleotides that are either endogenous or exogenous and/or heterologous with respect to the microorganism.

As used herein, "endogenous" with respect to genetic components of the microorganism means the genetic component (polynucleotide, regulatory element, promoter, or terminator) is present at a particular location in the genome of a native form of a particular organism. In contrast, "exogenous" as used herein with regard to genetic components means that the genetic component is not present at a particular location in the genome of a native (i.e., wild-type or naturally-occurring) form of a particular organism. For example, an exogenous genetic component may have either a native or a non-native polynucleotide sequence. A genetic component having a native polynucleotide sequence (i.e., a sequence that is present in the genome of the corresponding wild-type organism), would still be considered as an exogenous genetic component if it were present at a different location in the genetically engineered microorganism than the location of the same genetic component within the genome of the wild-type microorganism. For further clarity, a polynucleotide sequence that is native to a first microorganism species would be considered as exogenous if it were introduced into the genome of a second microorganism species, and vice versa.

As used herein, the term "heterologous" with respect to polynucleotides and polypeptides means that the sequences of the polynucleotides and polypeptides are not normally found in the corresponding native or wild-type microorganism that is being genetically modified.

In some implementations, the expression of one or more of the polynucleotides described herein may be placed under control of one or more regulatory elements (e.g., promoters, terminators, transcriptional enhancers, activators, or repressors, genetic switches). In some implementations, such regulatory elements (which may be exogenous and/or heterologous with respect to the microorganism) are operably linked to a polynucleotide described herein to enable control of its expression in response to changes in oxygen levels (e.g., an oxygen-sensitive promoter), intracellular or extracellular pH (e.g., a pH-sensitive promoter), nutrient concentrations (e.g., phosphate or nitrogen), the presence or concentration of an inducer (e.g., an inducible promoter), and/or a parameter controllable during fermentation (e.g., temperature, composition of the fermentation broth). In some implementations, a combination of different regulatory elements may be used to achieve differential expression of one or more polynucleotides described herein, for example, depending on the phase of the processes described herein (e.g., growth phase versus production phase). For example, expression of a polypeptide catalyzing the conversion of glycolate to glyoxylate can be increased during a growth phase, and subsequently decreased during a production phase, while expression of a polypeptide encoding a glycolate exporter may be decreased during the growth phase and subsequently increased during the production phase.

In some implementations, one or more of the polynucleotides described herein may by comprised in a plasmid, and/or integrated into the genome of the microorganism. Where the polynucleotides are comprised in a plasmid, the plasmid may further comprise one or more selection markers (e.g., antibiotic resistance genes) that enable selection and/or identification of positive transformants.

(a) Conversion of Ethylene Glycol to Glycolaldehyde

In some implementations, the microorganism may be genetically engineered (or genetically modified) for increased conversion of ethylene glycol to glycolaldehyde in the presence of oxygen (e.g., improved oxygen tolerance) as compared to a corresponding microorganism lacking the genetic engineering (or genetic modification). For example, the microorganism may be genetically engineered (or genetically modified) for improved oxygen-tolerant conversion of ethylene glycol to glycolaldehyde as compared to a corresponding microorganism lacking the genetic engineering (or genetic modification). As used herein, the expression "improved oxygen tolerant conversion" or "improved oxygen tolerance" relates a genetic modification that alleviates the negative effect of increased/increasing oxygen levels on the uptake and/or consumption of ethylene glycol by microorganism that, for example, relies on enzymes susceptible to degradation by metal-catalyzed oxidation.

In some implementations, the microorganisms described herein may comprise a polynucleotide encoding a polypeptide that catalyzes reaction (a), i.e., the conversion of ethylene glycol to glycolaldehyde, wherein the polypeptide comprises an enzyme of class E.C. 1.1.1, E.C. 1.1.3, or E.C. 1.1.5, or a functional variant or fragment thereof.

Enzymes belonging to E.C. 1.1.1 include oxidoreductases acting on the CH—OH group of donors with NAD(+) or NADP(+) as acceptor (Levin et al., 2004). Enzymes belonging to E.C. 1.1.3 include oxidoreductases acting on the CH—OH group of donors with oxygen as acceptor (e.g., oxidases such as alcohol oxidase or glycerol oxidase; Isobe, 1995; Isobe and Nishiseb, 1995). Enzymes belonging to E.C. 1.1.5 include oxidoreductases acting on the CH—OH group of donors with a quinone or similar compound as acceptor (e.g., a pyrroloquinoline quinone (PQQ)-dependent enzyme, such as from *Pseudomonas putida*; Muckschel et al., 2012).

As used herein, the expressions "functional variant" and "functional fragment thereof" refer to variants of polypeptides described herein that differ from a reference polypeptide by one or more amino acid substitutions, deletions, and/or insertions that do not abrogate the desired enzymatic activity of the polypeptide. For example, in some implementations, a functional variant may comprise one or more conservative amino acid substitutions of a reference polypeptide, or a functional fragment may comprise a truncation at the N and/or C terminus of a reference polypeptide without affecting for example a catalytic domain of the reference polypeptide.

In some implementations, a functional variant of a polypeptide described herein may have an improved property (e.g., improved enzymatic activity, stability and/or subcellular localization) over the reference polypeptide, for the purposes of the processes described herein (e.g., for enhanced glycolate production). For example, the functional variant (e.g., of a polypeptide catalyzing reactions (a) and/or (b)) may have reduced sensitivity (improved tolerance) to oxygen (e.g., to metal catalyzed oxidation).

In some implementations, the expression and/or activity of the enzyme that converts ethylene glycol to glycolaldehyde is oxygen-independent or has reduced oxygen-sensitivity (improved oxygen tolerance), for example as compared to a corresponding wild-type enzyme.

In some implementations, the polypeptide that catalyzes reaction (a) may comprise or consist of lactaldehyde reductase, also known as propanediol oxidoreductase E.C. 1.1.1.77, or a functional variant thereof. In some implementations, the lactaldehyde reductase may encoded by the gene fucO. In some implementations, the lactaldehyde reductase may comprise an amino acid substitution I7L and/or L8V or L8M, based on the amino acid numbering of the native lactaldehyde reductase encoded by fucO from *E. coli* MG1655. Such amino acid substitutions may improve the resistance of the enzyme to degradation by metal catalyzed oxidation, thereby reducing its sensitivity to oxygen.

Figure 9:
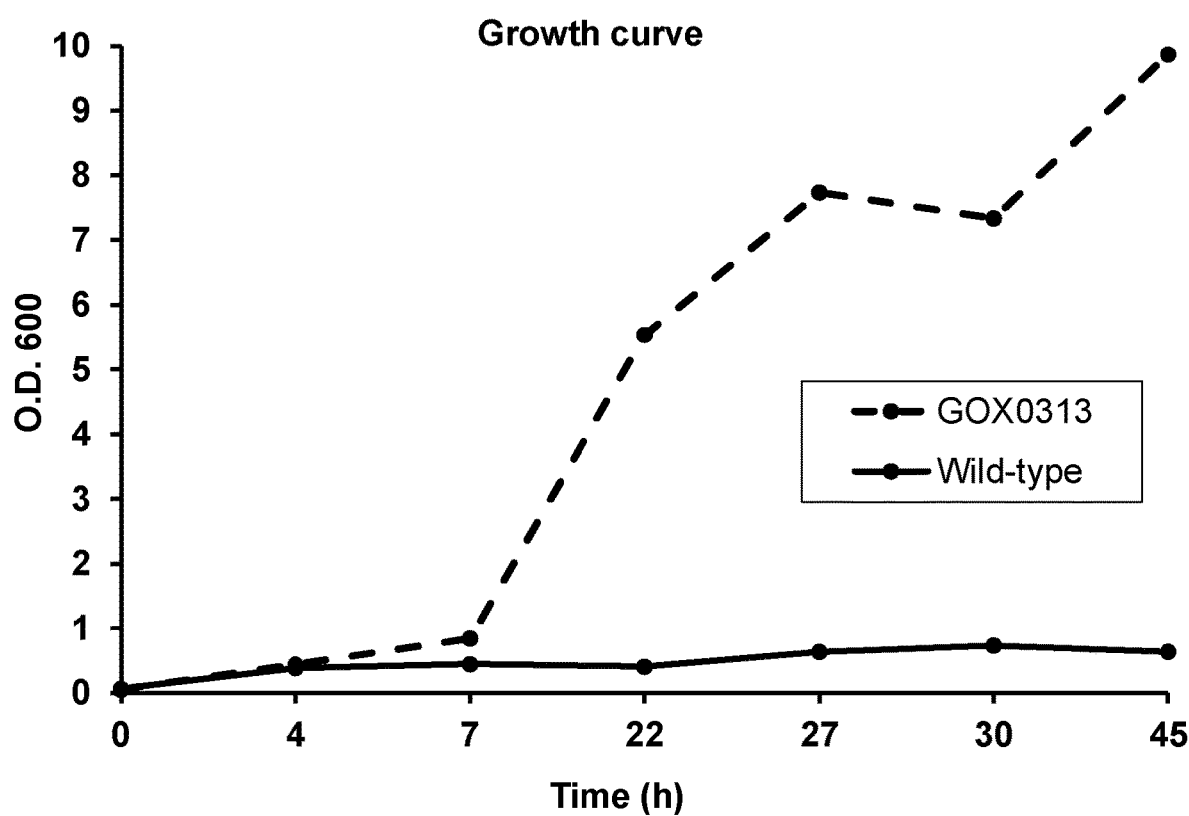
FIG. 9 is a graph of cell growth over time contrasting a wild-type *Escherichia coli* MG1655 strain to a corresponding strain expressing the ethylene glycol oxidizing Gox0313 enzyme that uses zinc as a cofactor instead of iron, as well as the glycolaldehyde oxidizing enzyme, aldA, when cultured in M9 minimal media supplemented with 20 g/L ethylene glycol and 0.1% yeast extract.

In some implementations, the polypeptide that catalyzes reaction (a) may comprise or consist of an enzyme that uses an oxygen-insensitive or oxygen less sensitive cofactor, such as a cofactor other than iron. In some implementations, the polypeptide that catalyzes reaction (a) may comprise or consist of an enzyme that uses zinc as a cofactor and/or the enzyme is or comprises as a zinc-dependent alcohol dehydrogenase (e.g., a cinnamyl alcohol dehydrogenase), such as the NAD-dependent alcohol dehydrogenase from *Gluconobacter oxydans* 621H set forth in Genbank accession: AAW60096, as shown in FIG. 9.

In some implementations, the expression of the polynucleotide encoding the polypeptide that catalyzes reaction (a) may be placed under the control of a constitutively active promoter.

In some implementations, expression of the polypeptide catalyzing reaction (b) may be deliberately controlled or attenuated to maintain the intracellular levels of glycolaldehyde to sub-toxic levels (e.g., by the use of a weak promoter, an inducible promoter, and/or low-copy number plasmid).

(b) Conversion of Glycolaldehyde to Glycolate

In some implementations, the microorganisms described herein may comprise a polynucleotide encoding a polypeptide that catalyzes reaction (b), i.e., the conversion of glycolaldehyde to glycolate, wherein the polypeptide comprises an enzyme of class E.C. 1.2.1, E.C. 1.2.3, or E.C. 1.2.5, or a functional variant or fragment thereof.

Enzymes belonging to E.C. 1.2.1 include oxidoreductases acting on the aldehyde or oxo group of donors with NAD(+) or NADP(+) as acceptor (e.g., aldehyde dehydrogenase; Brouns et al., 2006). Enzymes belonging to E.C. 1.2.3 include oxidoreductases acting on the aldehyde or oxo group of donors with oxygen as acceptor (e.g., aldehyde oxidase; Yamada et al., 2015). Enzymes belonging to E.C. 1.2.5 include oxidoreductases acting on the aldehyde or oxo group of donors with a quinone or similar compound as acceptor (e.g., a dehydrogenase; Klein et al., 1994; Zhang et al., 2003).

In some implementations, the polypeptide that catalyzes reaction (b) may comprise or consist of a lactaldehyde dehydrogenase (E.C. 1.2.1.22). In some implementations, the lactaldehyde dehydrogenase may be encoded by the gene aldA.

In some implementations, the expression of the polynucleotide encoding the polypeptide that catalyzes reaction (b) may be placed under the control of a constitutively active promoter.

In some implementations, expression of the polypeptide catalyzing reaction (c) may be deliberately controlled or attenuated to maintain the intracellular levels of glycolaldehyde to sub-toxic levels (e.g., via the use of a weak promoter, an inducible promoter, and/or low-copy number plasmid).

(c) Conversion of Glycolate to Glyoxylate

In some implementations, the microorganisms described herein may comprise a polynucleotide encoding a polypeptide catalyzing reaction (c), i.e., the conversion of glycolate to glyoxylate, wherein the polypeptide comprises an enzyme of class E.C. 1.1.3.15, or a functional variant or fragment thereof.

Enzymes of class E.C. 1.1.3.15 include oxidoreductases acting on the CH—OH group of donors with oxygen as acceptor. In some implementations, the polypeptide that catalyzes reaction (c) may comprise or consist of glycolate oxidase.

Figure 1A:
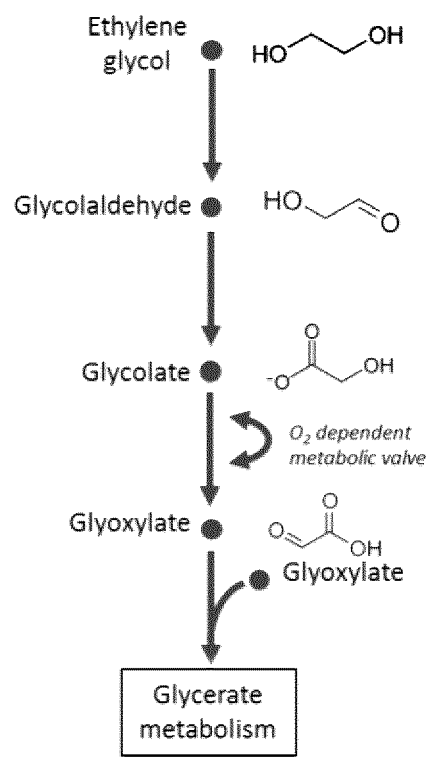
FIGS. 1A, 1B and 1C are diagrams showing metabolic conversion pathways of ethylene glycol (FIG. 1A), xylose (FIG. 1B), and glucose (FIG. 1C).
Figure 1B:
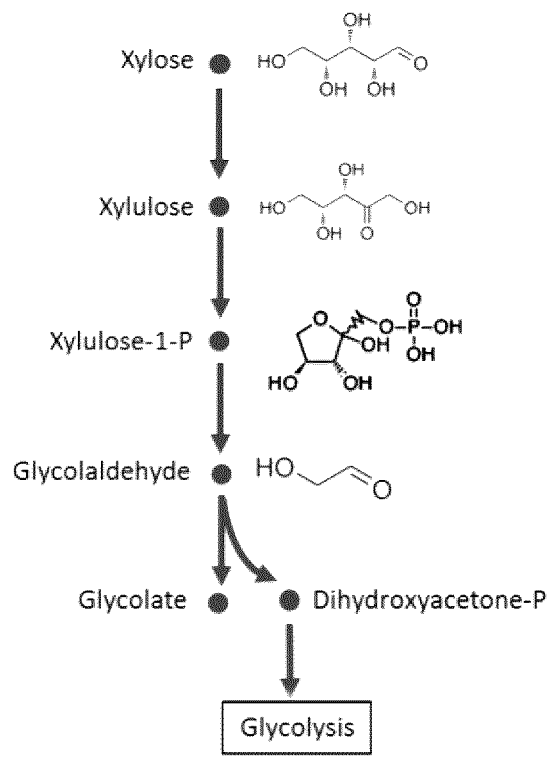
Figure 1C:
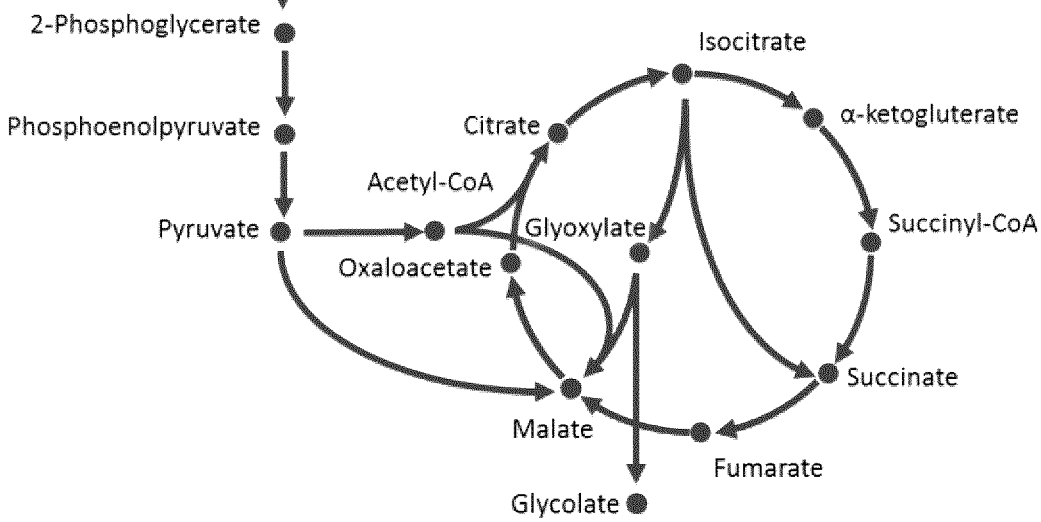

As indicated in FIG. 1, in some implementations, the oxygen-dependent enzymatic conversion of glycolate to glyoxylate acts as an oxygen-dependent metabolic valve that enables the microorganism to (1) utilize glyoxylate for cell growth (biomass accumulation) at higher oxygen concentrations in a growth phase, and (2) allow glyoxylate to accumulate under lower oxygen concentrations in a production phase.

In some implementations, the expression of the polynucleotide encoding the polypeptide that catalyzes reaction (c) may be placed under the control of a constitutively active promoter, an oxygen-sensitive promoter, a pH-sensitive promoter, or an inducible promoter. In some implementations, it may be advantageous to employ a strong and/or constitutively active promoter in order to maintain intracellular levels of glycolaldehyde to sub-toxic levels.

(d) Export of Glycolate Extracellularly

In some implementations, the microorganisms described herein may comprise a polynucleotide that encodes a polypeptide that catalyzes or facilitates reaction (d) the export of intracellular glycolate to the extracellular environment (e.g., into the fermentation broth). For example, some microorganisms may comprise a native glycolate exporter, and some microorganisms can be genetically modified to express an exogenous and/or heterologous glycolate exporter.

In some implementations, the polypeptide that catalyzes or facilitates reaction (d) may be annotated as a glycolate permease such as glcA from *Escherichia coli*, a formate permease such as focA from *Escherichia coli*, a lactate/glycolate symporter such as lldP from *Escherichia coli* or glycolate/glycerate transporter such as PLGG1 from *Arabidopsis thaliana* or a functional fragment or variant thereof.

In some implementations, it may be advantageous to express a polynucleotide encoding a fusion protein comprising enzymes that catalyze two or more reactions described herein (e.g., reactions (a) and (b), or (b) and (c)). Such fusion proteins are within the scope of the present description.

In some implementations, for example where glycolate is not the final product, it may be advantageous for the microorganism to convert glycolate to a downstream product of interest such as polyglycolic acid, ethanolamine, or glycine. In such implementations, the microorganism may be further genetically engineered to comprise one or polynucleotides encoding one or more enzymes for converting glycolate to polyglycolic acid, ethanolamine, and/or glycine. The microorganism may then also be further genetically engineered to express an exporter of polyglycolic acid, ethanolamine, or glycine that exports intracellular polyglycolic acid, ethanolamine, or glycine to the extracellular environment.

Various aspects, implementations, embodiments, features, examples, and experiments regarding the present technology will be described in further detail below.

Work, Findings & Experimentation

A detailed description of work, finding and experimentation that has been done in the context of the present technology and innovations, is provided below.

Brief Summary of Work and Findings

A considerable challenge in the development of bioprocesses for producing chemicals and fuels has been the high costs of feedstock relative to oil prices that make these processes uncompetitive with their conventional petrochemical counterparts. Hence, in the absence of high oil prices for a foreseeable future, which was the main driver for white biotechnology, there has been a shift in the industry to instead produce higher value compounds such as fragrances for cosmetics. Yet still, there is a need to address climate change and develop biotechnological approaches for producing large market, lower valued chemicals and fuels. In this work, ethylene glycol, a novel feedstock that has shown promise to address this challenge, was studied.

An E. coli was engineered to consume ethylene glycol and as a case study, for chemical production, glycolate production was examined. At the tested conditions, one positive example fermentation performance led to the production of 10.4 g/L of glycolate after 112 hours of production time. The results clearly suggest that oxygen concentration is an important factor in assimilation of MEG as a substrate. It was also found that the uptake rates for ethylene glycol are sufficient to satisfy commercial benchmarks for productivity and yield. Finally, the use of metabolic modelling shed light on the intracellular distribution through the central metabolism implicating flux to 2-phosphoglycerate as the primary route for MEG assimilation. Overall, the work described herein suggests that ethylene glycol is a useful platform for commercial synthesis of fuels and chemicals that may achieve economic parity with petrochemical feedstocks while sequestering carbon dioxide.

Introduction and Comments on Work

Biotechnological approaches to addressing climate change and the need to sequester carbon dioxide have focused on the development of microbial strains engineered to produce chemicals and fuels derived from renewable sources of sugar. Despite the considerable success at engineering these strains, the lack of many successes at the commercial scale belies the immense challenge in the financial viability of these technologies in the face of low oil prices and expensive feedstock costs. In response, non-sugar feedstocks have been put forward as alternatives to compete efficiently with glucose based bioprocesses. For example, methane and syngas fermentations are currently under intense study and are also the focus of commercial development[1-3]. Formate is another chemical that has been suggested as a replacement for glucose since it can be produced from carbon dioxide and because of its inherent compatibility with biological processes[4,5]. However, its utility as feedstock for biological processes suffers from a number of drawbacks. The most evident drawback is the absence of pathways for its assimilation in the metabolism of traditional workhorse organisms such as yeast or E. coli. The oxidized nature of the substrate also results in carbon loss to enable synthesis of NAD(P)H co-factors that support product and ATP formation, and the requirement for high transport rates into the cell to achieve productivities similar to glucose or xylose fermentation. Hence, while appealing, the technical challenges are numerous.

Nonetheless, this appeal arises from the fact that formic acid can be generated electrochemically from $CO_2$. A one electron pair reduction of one mole of $CO_2$ produces one mole of formic acid. However by tailoring the catalyst and the reduction potential, multi-electron reduction can be achieved and it is possible to produce a variety of different reduced carbon species[6]. Biological processes have been used to produce many of these same chemicals that are typically produced by the petrochemical industry including 1-propanol, acetate, ethylene, etc[7-9]. The work, here, uses the observation that like formate, these other chemicals that can also derived by the electrochemical reduction of $CO_2$ are feasible growth substrates for biological processes and this should merit their consideration as alternative feedstocks for bioprocesses.

In evaluating these substrates as potential replacements for glucose, it is important to recognize that many cannot be naturally catabolized by traditional industrial workhorses. Hence, similar to formate, the metabolic engineering of substrate utilization pathways is preferred for desired production performance.

Additionally, many of the potential replacements are toxic and not compatible with bioprocesses. Others, while technically feasible as inputs to biological processes, suffer from poor faradic efficiency or poor selectivity in electrochemical reactors[10-13]. Hence, after screening from a list of products that can be generated electrochemically, it becomes apparent that only a few can be realized as practical substitutes for glucose[6]. Finally, beyond toxicity and efficiency which can be evaluated in a relatively straightforward manner, evaluating the feasibility of a new substrate for bio-based chemical production can be obfuscated by how its utilization is linked to the highly interconnected metabolic network. Indeed, refactoring large metabolic pathways into heterologous hosts has proven challenging in the past[14]. One method that may help to explain why a new substrate performs poorly examines the metabolic pathway that supports a substrate for chemical production in relation to the cell's entire metabolism.

In an earlier study[22] this relationship was characterized by calculating the interactions between two competing objectives of cellular systems, growth and chemical production. The theory laid out how the underlying network structure gives way to growth independent chemical production. That relationship was captured by a mathematical framework using elementary flux modes to measure the interconnectedness of the cell system and the desired objectives. Hence, a metric was defined to measure the orthogonality of the chemical production pathways with respect to the biomass production.

It was found that the organization of ideal metabolic structures designed to minimize cell-wide interactions had a characteristic branched topology. This type of orthogonal structure could be exploited for two stage fermentation. Furthermore, an important finding from that study was glucose, while a common substrate for industrial fermentation, is not ideally suited for chemical production objectives due to the significant overlap between the pathways for biomass synthesis and chemical production. Instead, substrate selection should be based on the chemical targeted for production. Among the various substrates and products, it was identified that ethylene glycol was a highly promising substrate for orthogonal production of a variety of chemicals because it minimized the interactions between biomass and chemical producing pathways.

Therefore, among the variety of different chemicals that can be produced electrochemically, ethylene glycol is a promising, unconventional feedstock. It is produced today primarily by the petrochemical industry from ethylene. However, a process for making ethylene glycol from $CO_2$ has shown early promise, and is currently the focus of industrial scale up. In this regard, its utilization as a feedstock for biological processes is important because it can serve as a replacement for glucose in the modern bioprocess.

In the present work, an *E. coli* was engineered and characterized as a biocatalyst capable of consuming ethylene glycol as a carbon source, and its application as a novel substrate for industrial bioprocesses was explored. This platform for growth and chemical production was then applied to a case study for glycolic acid production. This case study attempts to validate an orthogonal approach for chemical production, relating the network topology and two-stage fermentation. Conventional approaches to glycolic acid in *E. coli* have instead focused on using glucose as the substrate, and implementing genetic strategies that couple production to growth. Several studies have been published that have examined glycolic acid production from glucose[15,16] and xylose[17-19]. The highest of these reports achieves titers of 56.44 g/L and a yield of 0.52 g/g[20]. To our knowledge, only three studies have examined ethylene glycol conversion to glycolic acid as a biotransformation[21-23]. However, in this work the metabolism and growth physiology of *E. coli* growing on ethylene glycol were thoroughly characterized. It was found that while growth rate is markedly slow relative to growth on glucose with a doubling time of 3.85 hours on ethylene glycol, that the substrate uptake rate is sufficiently high at up to 5 mmol/gDW-h to be relevant for industrial production. Glycolate, which required micro-aerobic conditions, reached titres of 10.4 g/L at a maximum theoretical yield of 66%. Overall, it was found that understanding the growth characteristics of the cell and a model on glycolate production shows that using ethylene glycol has potential for replacing glucose in industrial bioprocesses in applications where $CO_2$ streams and renewable electricity are available.

Materials and Methods

Media and Cultivation Conditions

Cells were grown using lysogeny broth (LB) as per manufacturer's instructions (Bioshop, Burlington, ON) for all strain construction and fermentation pre-cultures. When characterizing strains, cells were grown under M9 minimal media with the following compositions: 1.0 g/L NH4Cl, 3.0 g/L $KH_2PO_4$, 6.8 g/L Na2HPO4, 0.50 g/L NaCl. Supplements of yeast extract at 2 g/L were added to minimal media. Ethylene glycol was used as the carbon source as concentrations described in the text. IPTG was used at a concentration of 1 mM when necessary. A trace metal solution was prepared according to the following composition prepared in 0.1 M HCl per litre and added at a concentration of 1/1000: 1.6 g $FeCl_3$, 0.2 g $CoCl_2.6H_2O$, 0.1 g $CuCl_2$, 0.2 g $ZnCl_2.4H2O$, 0.2 g $NaMoO_4$, 0.05 g $H_3BO_3$. 1 M $MgSO_4$ and 1 M $CaCl_2$ was also added to the media at a concentration of 1/500 and 1/10,000, respectively. For all cultures, carbenicillin was added as appropriate at 100 µg/mL. Cells were grown in 250 mL shake-flasks for all characterization experiments and in bioreactors as described.

Culturing Techniques in Reactors

Pre-cultures were grown in LB rich media in 10 mL test tube cultures overnight and transferred fresh shake-flaks containing LB, 1 mM IPTG and 10 g/L ethylene glycol. After 24 hours, these cells were harvested by centrifugation, re-suspended in 2 mL of residual supernatant and used as inoculum for bioreactor or minimal media shake-flasks for characterization at 37° C.

Applikon MiniBio500 fermentation vessels were used for cultivating strains in bioreactors. Dissolved oxygen and pH probes were used in accordance with the manufacturers operating guidelines. M9 minimal media was used for cultivation in the bioreactor. pH was maintained at 7 with the addition of 3N KOH. Growth conditions were maintained at 37° C. Dissolved oxygen was maintained as described in the text. Flowrate was controlled as described using a Books Instruments mass flow controllers (GF Series) and gas was analyzed using Thermo Scientific™ Sentinel dB mass spectrometer for online gas measurement.

Analytical Methods

Analysis of fermentation production was measured via high performance liquid chromatography (HPLC). A Biorad HPX-87H organic acids column with 5 mM $H_2SO_4$ as the eluent and a flowrate of 0.4 mL/min at 50° C. was used. Organic acids were detected at 210 nm. Cell densities of the cultures were determined by measuring optical density at 600 nm (GENESYS 20 Visible Spectrophotometer). Cell density samples were diluted as necessary so as to fall within the linear range. A differential refractive index detector (Agilent, Santa Clara, Calif.) was used for analyte detection and quantification. Yields were calculated between two time points, whereas the cumulative yield was calculated between the initial and final measurements.

Plasmids and Strains fucO and aldA were cloned from *E. coli* MG1655 genomic DNA and assembled using Gibson Assembly[24] into a pTrc99a vector. Ribosome-binding site (RBS) sequences were placed onto the overhang of the forward primer. AACAAAATGAGGAGGTACTGAG was the RBS sequence used in front of aldA. AAGTTAAGAGGCAAGA was the RBS sequence used in front of fucO. The Trc promoter was used to drive expression. Wild-type strains of *E. coli* MG1655 were obtained from the *Coli* Genetic Stock Centre (Yale).

Flux Balance Analysis

Flux balance analysis (FBA) was performed using MATLAB R2015a installed with COBRA 2.0 toolbox and using the GLPK linear solver (GNU Project). The genome scale model iAF1260 was used to perform all modelling. The ATP maintenance reaction was left unchanged at a value of 8.9 mmol/gDW-h. The model was modified by adding a reaction for converting ethylene glycol to glycolaldehyde using NAD cofactors. Transport of ethylene glycol was modelled as free diffusion and no proton translocation was included as part of its exchange reaction. Initial characterization of the cell to model the respiratory quotient was only constrained by its substrate uptake rate which was measured at 5 mmol/gDW-h. More detailed intracellular flux data was extrapolated by constraining substrate uptake rate as well as glycolate production rates and oxygen uptake rates as determined by analysis of the off-gas from the process mass-spec during bioreactor cultivation.

Results

Ethylene Glycol is a Preferred Substrate Over Formate

In an earlier study, orthogonality was identified as a metric to assess and design efficient metabolic networks for the production of chemicals. That study defined orthogonality as a quantitative measure of the interconnectedness between pathways that produce a target chemical and biomass. The principal focus of that work was to examine how metabolic pathway organization influences chemical production. In this first section, that methodology was applied to compare formate and ethylene glycol utilization, both of which can be synthesized electrochemically. Also assessed was the specific role that substrate selection has on five different chemicals that are important to industry found in Table 1. This analysis allows us to implicitly account for metabolic constraints such as redox and ATP. Glycolic acid showed the highest orthogonality score between all the substrate product pairs, and hence was selected as the demonstration product for production from ethylene glycol.

TABLE 1

|  | Succinate | | Ethanol | | Glycolate | | 2,3-Butanediol | |
| --- | --- | --- | --- | --- | --- | --- | --- | --- |
|  | Score | Yield | Score | Yield | Score | Yield | Score | Yield |
| Formate | 0.47 | 0.29 | 0.50 | 0.14 | 0.48 | 0.33 | 0.49 | 0.18 |
| Ethylene glycol | 0.54 | 0.95 | 0.61 | 0.62 | 0.67 | 1.22 | 0.66 | 0.66 |
| Glucose | 0.41 | 1.12 | 0.44 | 0.51 | 0.41 | 0.85 | 0.47 | 0.50 |
| Xylose | 0.36 | 1.11 | 0.36 | 0.65 | 0.34 | 0.65 | 0.40 | 0.64 |

Table 1 shows the orthogonality score for these chemicals using ethylene glycol and formate as carbon sources. Glucose and xylose are also included in the calculations as they provide a reference against the conventional bio-process. For all chemicals, the orthogonality score is larger for ethylene glycol than formate and less substrate is required to produce the same quantity of product as well. Table 1 thus relates to yield and orthogonality metrics for chemical production from different substrates. The orthogonality scores for various products are shown comparing two substrates that can be generated electrochemically against conventionally used substrates by their natural pathways. Formate has orthogonality scores similar to many sugar-consuming pathways, indicating a relatively complex and inter-connectedness for its utilization. The highest scores are those for ethylene glycol with yields that are better than the sugars glucose and xylose. Yield is given as g of product per g of substrate.

The orthogonality metric is a mathematical measure of the set of interactions that each substrate assimilation pathway has to the cell components outside their pathways. Hence, it implicitly measures the biological complexity one might expect to ensure that the biomolecular machinery of that pathway can concurrently function within the cell's natural metabolism to support biological and chemical production objectives. Analysis of the metabolism of formate shows its low score arises from its low degree of reduction which requires flux through the TCA cycle to generate the necessary reducing equivalents for growth and energy, irrespective of what chemical is produced. The low degree of reduction is also the reason for low product yields. Hence, this line of network analysis suggests ethylene glycol is a superior substrate to formate in E. coli. Given higher scores for ethylene glycol utilization, it was resolved that ethylene glycol utilization was promising and these results were compared to sugar metabolism in E. coli for glycolic acid production.

Glycolate is an alpha-hydroxyacid used in the synthesis of a variety of different plastics and polymers, cosmetics and industrial detergents. Currently, metabolic engineering has established routes to glycolic acid from glucose and from xylose. Theoretical yields have been dependent on both the substrate selected as well as the biosynthetic pathway used for production. Examples of glycolate production from glucose in literature has primarily been demonstrated by the activation of the glyoxylate shunt.

Regarding FIG. 1, it is noted that glycolate can be produced by a variety of different substrates. Ethylene glycol conversion to glycolate is shown in (A). The two most commonly studied substrates for production are xylose (B) and glucose (C). To efficiently produce glycolate from glucose or xylose, genetic interventions are required to the central metabolism to couple growth and glycolate synthesis. The focus of this study examines ethylene glycol consumption. Limiting oxygen provides a mechanism to permit glycolate accumulation. Under fully aerobic conditions, glycolate is converted to glyoxylate and channeled to the central metabolism for growth via the glycerate metabolism. Under oxygen limiting conditions, glycolate accumulates.

FIG. 1 shows glycolate production from three different pathways. Production from glucose is highly coupled to biomass synthesis, and exhibits the lowest orthogonality score, 0.41. Glycolate production from xylose has also been demonstrated by the use of a synthetic pathway for xylose assimilation in E. coli. While this pathway fits partly into an orthogonal criterion for glycolate production, the concomitant production of pyruvate for every mole of glycolate requires the use of the cells highly interconnected glyoxylate cycle to reach theoretical yields. The orthogonality score, for this reason, is comparatively smaller. The largest orthogonality score of 0.67 was found for the case where ethylene glycol served as a substrate. Bioconversion of ethylene glycol to glycolate fits into the ideal network architecture that follows a branched pathway. Under oxygen limiting conditions, the reaction that consumes glycolate, catalyzed by glycolate oxidase, can be limited, and the cell can accumulate glycolate. These results show that ethylene glycol as a substrate is more orthogonal than traditional substrates and hence suitable for validating as a concept of orthogonal pathways based design.

Ethylene Glycol Utilization by E. coli

There exist pathways in nature that allow microorganisms to consume ethylene glycol as a carbon source[25-28]. While not commonly reported in metabolic engineering applications, these organisms use one of two types of metabolic pathways. The first pathway utilizes a diol-dehydratase resulting in the dehydration of ethylene glycol to acetaldehyde. Acetaldehyde is then activated to acetyl-Coa by an acetaldehyde dehydrogenase enzyme which provides the cell with the key precursor metabolite to support growth via the TCA cycle and gluconeogenic pathways. The production of one mole of acetyl-Coa from one mole of ethylene glycol concomitantly produces one NADH. This pathway is most commonly found in some Clostridium species and a few other anaerobic organisms owing to the oxygen sensitivity of the diol-dehydratase[25,27]. The second mode of ethylene glycol degradation utilizes a pathway wherein ethylene glycol is successively oxidized using nicotinamide cofactors and oxygen to produce glyoxylate. Glyoxylate which is a gluconeogenic carbon substrate, can then be used as the growth metabolite as it enters lower glycolysis at the 2-phosphoglycerate node as well as the TCA cycle via the glyoxylate shunt.

Wildtype E. coli MG1655 cannot naturally grow on or degrade ethylene glycol. However, it is possible to select for this strain, and to our knowledge, only one study has ever reported ethylene glycol utilization by E. coli.[29] That strain was selected from derivatives of propylene glycol utilizing mutants. Researchers identified increased activities of glycolate oxidase, glycolaldehyde dehydrogenase and propanediol oxidoreductase as the necessary components required for its assimilation. More generally, a survey of the literature shows that enzyme promiscuity is a relevant element of the utilization of alcohols[22,23]. In this specific case, enzymes regarded as being important for propanediol or even glycerol utilization across many organisms have shown activity on ethylene glycol and are regarded as the key methods for degradation, irrespective of the dehydratase route or the oxidative route via glyoxylate[26-28]. Hence, in this study, to engineer E. coli the native gene fucO and aldA that have been established as key enzymes supporting propanediol utilization in E. coli, were overexpressed. Since FucO has previously been shown to be sensitive to oxygen via metal catalyzed oxidation that results in the inactivation of $Fe^{2+}$ dependent propanediol oxidoreductases, two variants of the pathway to consume ethylene glycol were designed. In variant 1 (strain LMSE11), the mutated version of fucO was used wherein I7L and L8V based on earlier mutagenesis studies[30]. In the second variant (strain LMSE12), L8M was used because it was also suggested to play a role in alleviating metal catalyzed oxidation (MCO) toxicity in propanediol assimilation by E. coli. Both variants had the same ribosome binding site and trc promoter upstream of the start codon.

Cells were grown aerobically in M9 minimal media with ~10 g/L ethylene glycol, supplemented with 0.2% yeast extract in 250 mL shake flasks. Fermentation profiles between the two strains constructed were markedly different. LMSE11 completely consumed ethylene glycol in 47 hours while LMSE12 had consumed only ~10% of the initial substrate in same time period with 10 g/L as residual MEG. These results are shown in FIG. 2.

Figure 2:
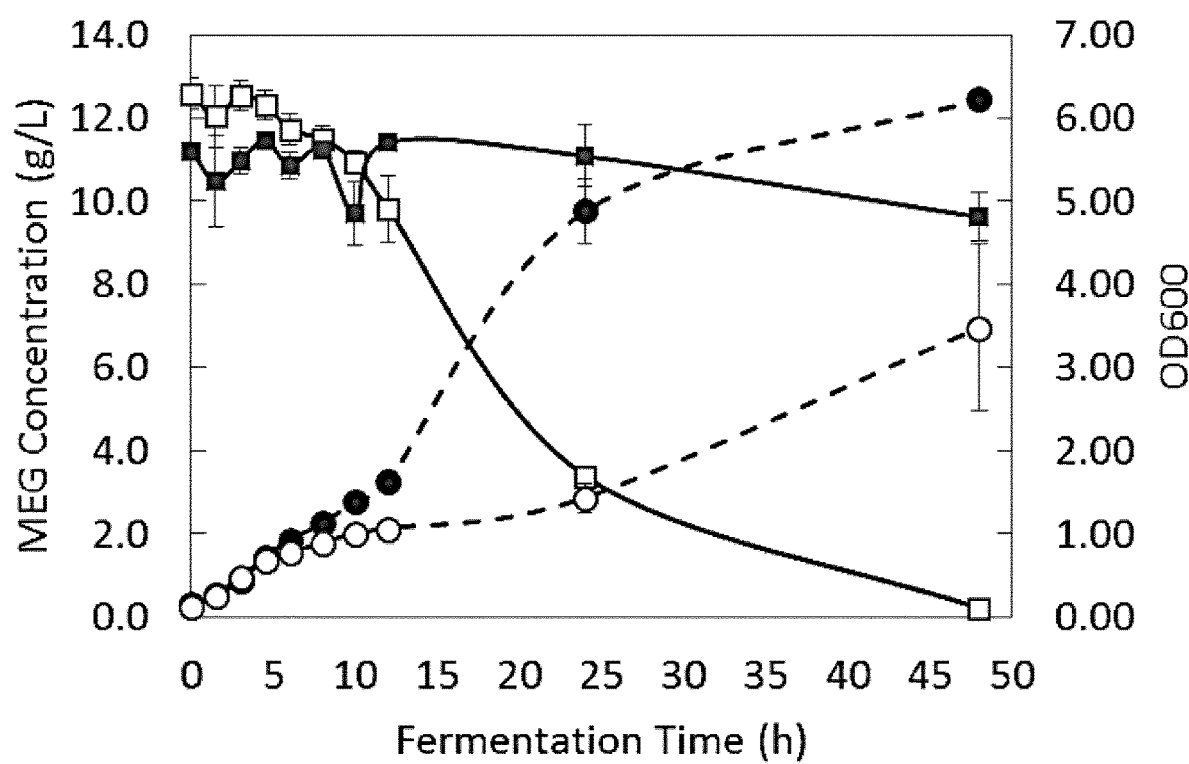
FIG. 2 is a graph of cell growth and substrate consumption over time, particularly MEG concentration and $OD_{600}$ versus fermentation time.

FIG. 2 illustrates cell growth curves and their substrate consumption profiles for the strains constructed in this study. The oxygen variants of fucO showed a marked difference in growth rate and substrate utilization in shake-flask experiments. Ethylene glycol consumption is shown by the dashed lines and $OD_{600}$ is depicted by the solid lines. Yellow (light) shows strain LMSE11 while green shows LMSE12. Error bars indicate standard deviation of triplicate experiments.

Growth yield for LMSE11 was calculated to be 0.28 gDW/g MEG. Flux balance analysis via in silico simulations of the core model of E. coli revealed the theoretical yield to be 0.35 gDW/g MEG. These results seemed to be in reasonable agreement with theoretical yields for biomass synthesis, suggesting that two genes are sufficient to efficiently convert ethylene glycol to biomass using E. coli's natural biosynthetic pathways. The substrate uptake rate in shake-flasks was determined to be 5 mmol/gDW-h. The experimental growth rate was calculated to be $0.18\ h^{-1}$ corresponding to a 3.85 hour doubling time. FIG. 2 shows the growth curve and substrate utilization of for both variants. LMSE12 consumed substantially less ethylene glycol and had residual ethylene glycol concentrations just under 10 g/L in the same time period.

Analysis of the fermentation media by HPLC showed the absence of fermentation products like acetate or lactate, and the intermediate metabolites glycolaldehyde and glycolate. However, since LMSE11 showed higher utilization rates, it was decided to pursue that variant further.

Orthogonal Production of Glycolate by E. coli

Having established ethylene glycol consumption by an engineered strain of E. coli, the use of ethylene glycol as an orthogonal substrate for the production of glycolic acid was explored. E. coli strain LMSE11 was grown in bioreactors with minimal media, supplemented with yeast extract at 2 g/L and sparged with air to maintain oxygen at 1 v/vm (300 mL/min). These conditions ensured that oxygen saturation above 50%. Cells were initially grown overnight for 18 hours for growth in LB rich media supplemented with ethylene glycol and induced with IPTG. After overnight growth, they were centrifuged, washed and suspended in minimal media and inoculated to bioreactors at an OD~0.4 (approx. 0.23 gDW/L). The bioreactors contained 1 mM IPTG to maintain induced expression of MEG utilization genes to support biomass.

Figure 3A:
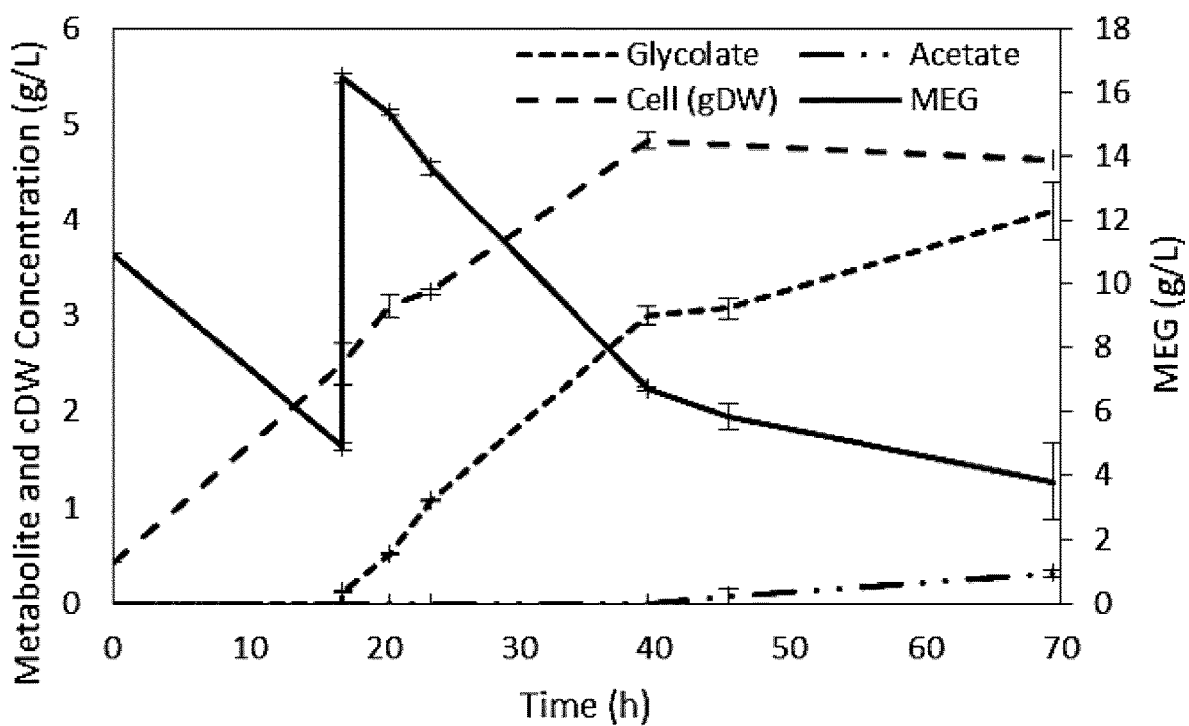
FIGS. 3A and 3B is a pair of graphs showing the influence of aeration on glycolate production, particularly metabolite and cDW concentration as well as MEG versus time.
Figure 3B:
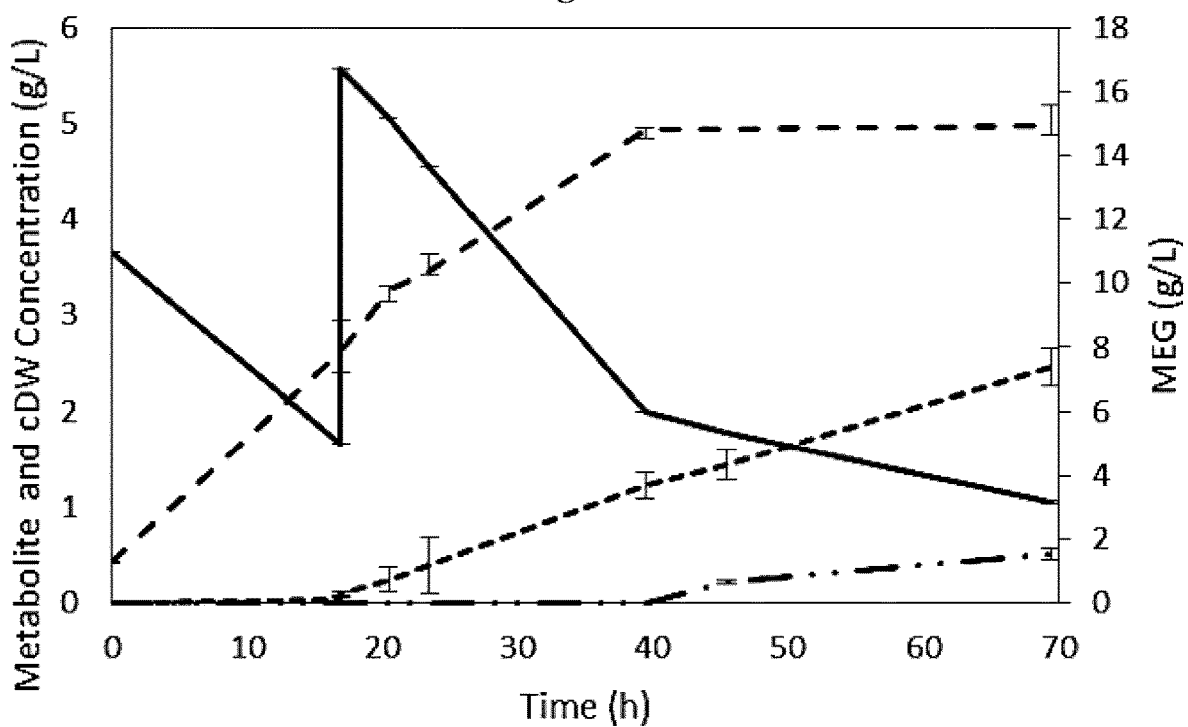

At 20 hours, the aeration was reduced to 150 mL/min (0.5 v/vm) and 50 mL/min (0.16 v/vm) to simulate high and low aeration rates, and the impeller agitation was dropped to 500 rpm. It was observed that cell growth continued until approximately 40 hours reaching approximately 5 gDW/L at which point cells in both reactors appeared to reach a stationary phase. Production of glycolate, however, was continued for 30 hours more after the beginning of stationary phase at which point the fermentation was stopped. Cells grown at a higher rate of aeration accumulated more glycolate by the end of the batch. The final glycolate titres for the two treatments were 2.5 g/L and 4.1 g/L. Using flux balance analysis to approximate carbon loss from respiration and accounting for cell growth and other products, it was possible to close the carbon balance at 83% and 88%, respectively. Average mass yield for glycolate on MEG measured during the production phase was 0.18 g/g and 0.32 g/g. FIG. 3 illustrates results of these experiments.

Referring to FIG. 3, influence of aeration on glycolate production is illustrated. To assess the impact of oxygen transfer in bioreactors, cells were grown under two aeration rates during the micro-aerobic phase of the fermentation. (Top) High aeration had a flow rate of 150 mL/min. (Bottom) Low aeration was characterized by flow at 50 mL/min. Experiments were conducted in duplicate. Error bars indicate range of the measured values.

Counter-intuitively, the lower aeration led to lower glycolate titers even though FucO in the MEG utilization pathway was expected to be sensitive to higher oxygen levels. However, this result can be explained by the fact that oxygen is required for the regeneration of NAD which is a substrate for the MEG utilization pathway. Hence, lower oxygen concentrations could lead to lowered flux through this pathway resulting in lower titers. These results suggest a trade-off between the oxygen sensitivity on the one hand and the requirement for oxygen as a substrate in the pathway. Next, it was desired to analyze the role of oxygen further using metabolic modeling and by increasing the aeration rate even further to see if glycolate production could be enhanced.

Dissolved Oxygen and Control Over Metabolism

To gain further insight into control of the cell's metabolism using oxygen and refine our approach to glycolate production, flux balance analysis (FBA) was used to simulate the intracellular flux through the central metabolism at 5 mmol/gDW-h which was determined with the shake-flask experiments. The simulations were constrained using the substrate uptake rate to approximate E. coli growth during the early exponential growth phase measured in shake flasks. The ATP maintenance flux was approximated at 8.9 mmol/gDW-h, a value experimentally used for glucose metabolism. The simulated flux distributions revealed a highly reorganized central metabolism of E. coli using gluconeognic pathways.

Figure 4:
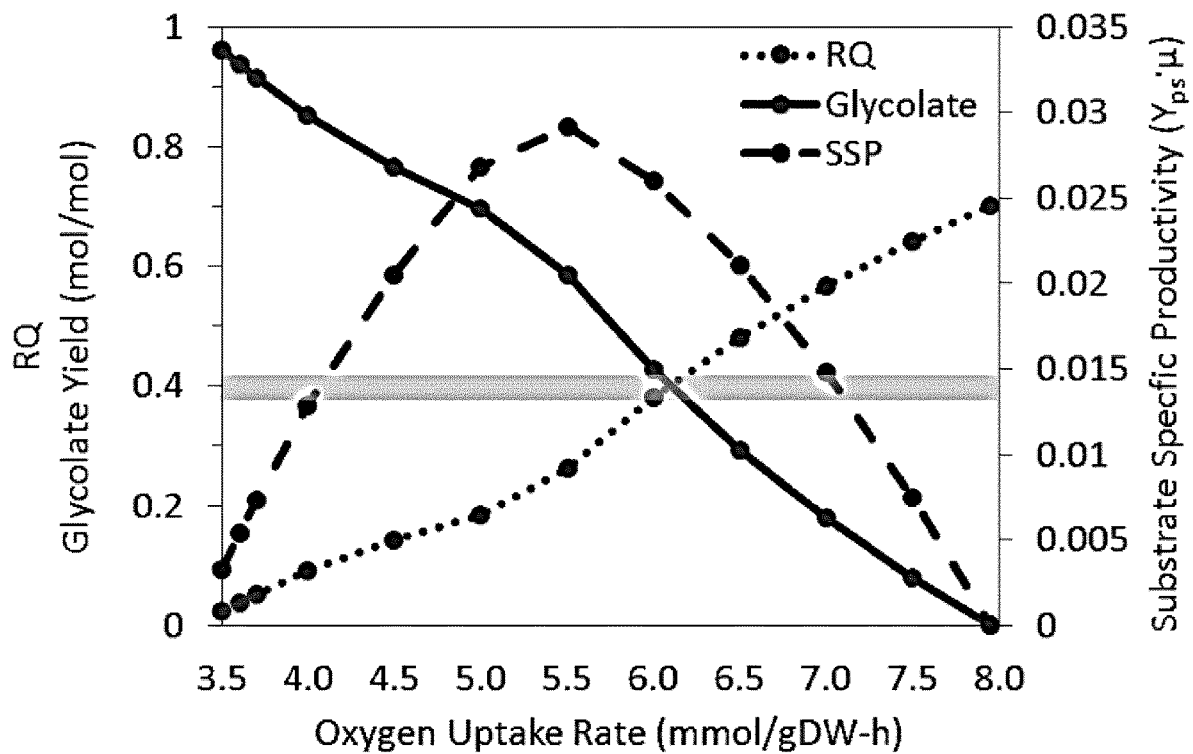
FIG. 4 is a graph showing metabolic modelling of glycolate production, in particular glycolate yield (glycolate, solid), respiratory quotient (RQ, dotted) and substrate specific productivity (SSP, dashed) versus oxygen uptake rate, modelled using flux balance analysis (FBA).

Under oxygen limiting conditions FBA predicts the observed fermentative cell behavior and glycolate accumulation. Then, this observation was explored further by modelling the production of the glycolate (as yield) by the cell and its respiratory quotient as a function of the oxygen uptake rate. This analysis allowed us to implicitly correlate the flowrate of air into the reactor to the metabolite production yields since the specific oxygen uptake is a function of air intake. FIG. 4 shows that the increase in glycolate yield and the onset of fermentation as oxygen uptake rate is reduced. These yields correlate with the respiratory quotient (RQ) that also decreases at a lower oxygen flux and increases with increasing oxygen flux before it levels off at saturating conditions. These results suggest that RQ is an important variable that can be monitored and controlled to optimize for glycolate production in real-time. Hence, this approach was used to control glycolate production in subsequent runs by ensuring that there was sufficient aeration.

Regarding FIG. 4, a graph related to metabolic modelling of glycolate production is shown, where glycolate yield (glycolate, blue), the respiratory quotient (RQ, green) and the substrate specific productivity (SSP, red) were modelled using FBA. Glycolate production begins at the onset of oxygen limitation which occurs at approximately 8 mmol/gDW-h of oxygen. At greater values, the RQ plateaus as sufficient oxygen as available for complete respiration and FBA predicts no glycolate accumulation. The grey bar indicates the values at which RQ was controlled experimentally during the production phase in later batches.

Glycolate Production and Fed Batch Strategy

Finally, given that it was possible to produce glycolate, further experiments were performed to attempt to improve glycolate production yield and increase titres. Based on what was learned from the initial fermentations, it was sought to increase the glycolate production phase and reduce the biomass production phase. This was achieved by increasing the aeration rate to 2 v/vm (600 mL/min) during the growth phase of the batch to prevent glycolate accumulation and divert as much flux towards biomass. In the second phase, the aeration rate was dropped to 100 mL/min. Results of this strategy are shown in the FIG. 5A. Final glycolate titres reached 6.8 g/L after approximately 70 hours production time with an initial production phase biomass concentration of approximately 4 gDW/L, corresponding to an average productivity 0.1 g/L-h or approximately 0.32 mmol/gDW-h. The initial yield of glycolate was 0.92 g/g after the first sample was taken, however, the cumulative yield decreased during the production course of the batch with the final overall production yield of 0.75 g/g or 61% of theoretical.

It was observed from these conditions that while significantly more product was produced at a higher yield, the cells took much longer to reach a concentration appropriate for a production phase. Whereas when the aeration rate was 1 v/vm in earlier batch, the cells reached a concentration of 4 gDW/L within 30 hours. However, at 2 v/vm it took almost 70 hours to reach the same concentration. It was hypothesized the longer time to reach a higher OD was likely due to increased dissolved oxygen levels and faster oxygen mass transfer rates to the cells during early exponential phase. Given the sensitivity of FucO to oxygen, in even the mutant variant, these two factors likely created an oxygen toxicity on the cells resulting from the inactivation of these proteins by metal-catalyzed oxidation and placing a high metabolic burden on the cell in regards to high protein demand without a sufficient means to utilize ethylene glycol as a carbon source.

Oxygen requirements is also one of the factors that affects the industrial production of biochemicals since it is a key component of operating costs which are determined by the energy inputs. One of the significant energy inputs for a process is the energy needed to aerate a bioreactor. In an earlier experiment, it was found that counter-intuitively, a higher aeration resulted in higher glycolate titres at a higher yield but that high aeration also retards cell growth. From a process perspective, it is desirable to operate a reactor at a lower flow rate. Building on all these earlier studies and the various competing objectives it was attempted produce glycolate at a high titre but at a lower aeration rate. Hence, cells were grown under a constant aeration 0.16 v/vm (50 mL/min), but during the production phase, the impeller speed in the reactor was dropped until the RQ, as measured by the online mass-spec read ~0.4. The working hypothesis based on FBA simulations was that this would achieve a yield greater than 0.4 mol/mol and place the production phase in near its maximum substrate specific productivity. The shaded region in FIG. 4 shows the range of the RQ measured during the course of the production phase as determined by three standard deviations from the average value. The average RQ was measured to be 0.37. The results of this experiment are shown in FIG. 5B. It was possible to reduce the biomass production phase to 26 hours, and produce 10.4 g/L of glycolate over a 112 hours production phase. The overall yield was determined to be 0.8 g/g from ethylene glycol corresponding to a molar yield of 0.66 mol/mol. The productivity was comparable to earlier experiment at 0.1 g/L-h. These experimental results were in line with and correlated well with FBA predictions for using RQ as a control variable. As the batch entered the glycolate production phase, it was observed a drop in the RQ. However, the measured RQ value of 0.37 corresponded to a production yield of 0.66 mol/mol—higher than the expected yield of 0.40 mol/mol. The results imply that while the general agreement between experimental data and FBA simulations are useful in establishing a control mechanism for fermentation on ethylene glycol, further optimization of model parameters is required to accurately predict physiological response to the environmental conditions. In particular, it was found that substrate uptake rate was reduced substantially in vivo however (approximately 0.7 mmol/gDW-h), which was not accurately captured by the FBA models (at 3.5 mmol/gDW-h).

Figure 5A:
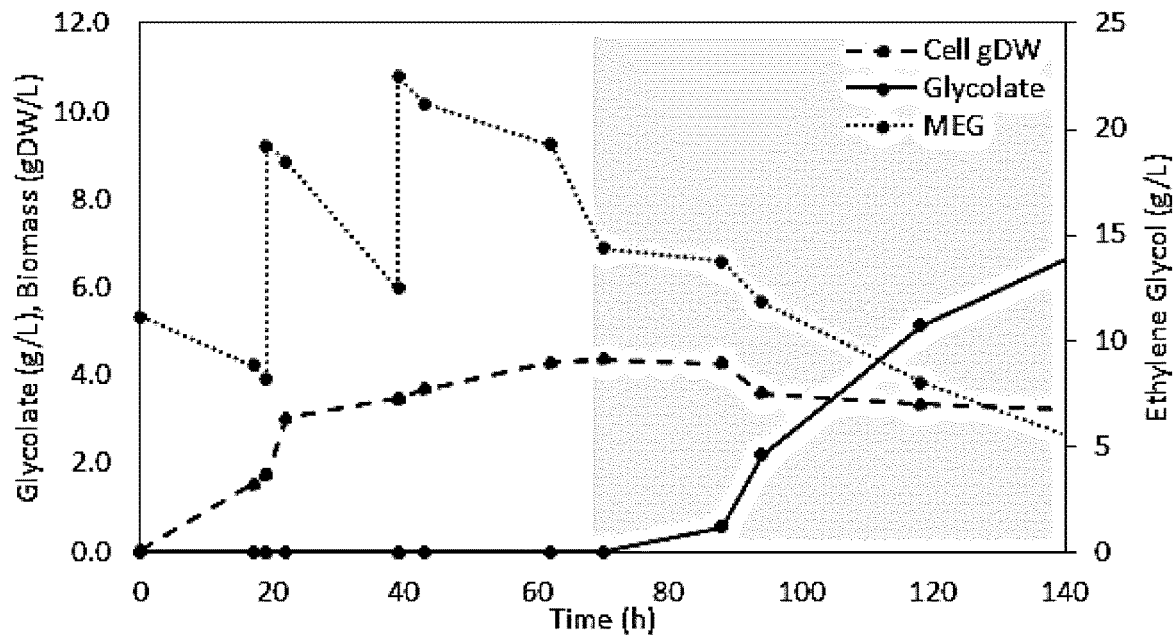
FIGS. 5A and 5B are a pair of graphs that relate to fermentation profiles for fed batch strategies, particularly showing glycolate, biomass and ethylene glycol concentrations versus time.
Figure 5B:
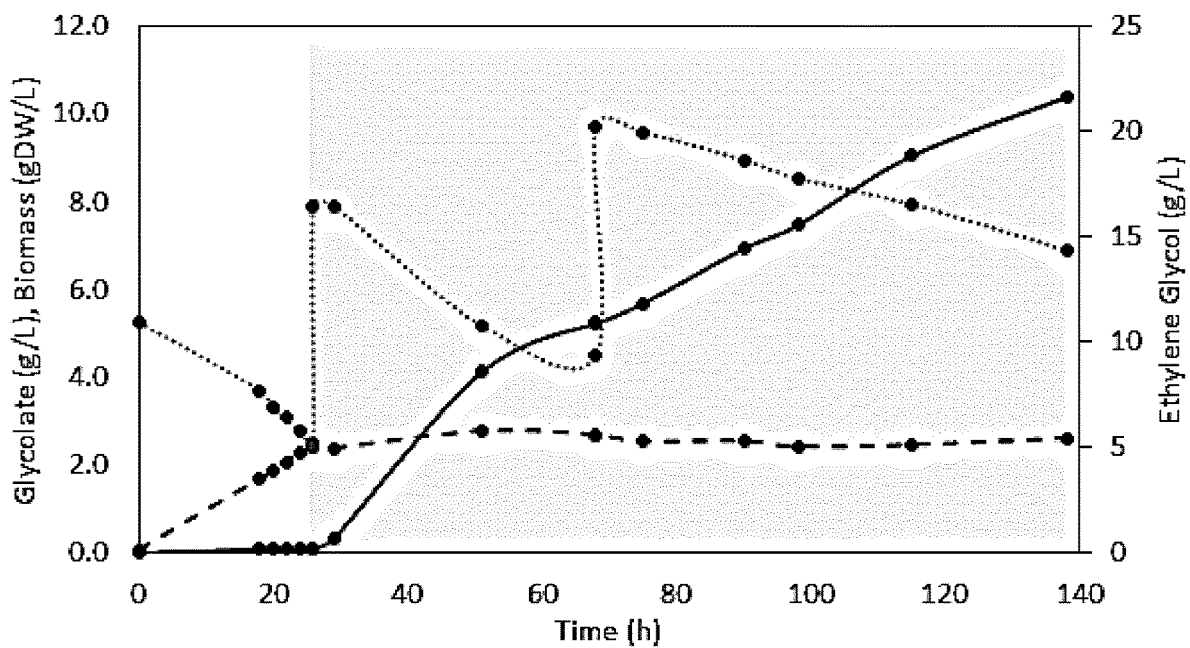

Regarding FIGS. 5A and 5B, which relate to fermentation profiles for fed batch strategies, fed batch studies were conducted to assess the long term stability of the production phase. The production phase is separated from the growth phase by grey shading. (A) Shows bioreactor conditions at 2 v/vm during the growth phase and 0.33 v/vm during the production phase at a cell density corresponding to 4 gDW/L. (B) Cells were grown at 0.167 v/vm air flow rate into the bioreactor with an average stationary phase cell density at 2.5 gDW/L. Cells were capable of robust glycolate production for well over 100 hours in the production phase.

Metabolic Flux Analysis Using E. coli Model

To gain insight into the intracellular fluxes of the cell, mass spec and HPLC data were used to constrain a genome scale model of E. coli and perform flux balance analysis. The model was then used to estimate the intracellular fluxes under ethylene glycol growth conditions to gain insight into the cellular metabolism. It was determined that ethylene glycol enters the metabolism at the glyoxylate node (FIG. 6 A). 70% of the glyoxylate production flux is channeled towards 2-phosphoglycerate (2PG) under aerobic conditions which enters lower glycolysis. The remaining glyoxylate is used to generate malate via malate synthase. It appears from the simulations that majority of the malate and 2PG generated by these pathways ends up in the TCA cycle. As a percentage, 65% of the total carbon entering the cell as ethylene glycol gets channeled into acetyl-coa. Conversely, about a fifth of the total carbon get channeled by gluconeogenic pathways towards upper glycolysis and the pentose phosphate pathways.

During the growth phase it was also observed small amounts of glycolate. The accumulation of glycolate suggested insufficient oxygen and thus the possibility that anaerobic pathways in the cell may be induced. Indeed trace amounts of formate were detected as peaks in the HPLC chromatogram.

Given that the 2PG pathway that assimilates ethylene glycol results in carbon loss via the tartronate semi-aldehyde carboligase step, simulations were performed to determine whether the glyoxylate cycle was sufficient for supporting cell growth by removing the reaction glyck2 (glycerate kinase) from the model. Removal of glyoxylate carboligase from the genome scale model showed a 50% decrease in the in silico growth rate. In contrast, experimental work on gene deletions in the same pathway show that it abolishes growth on glycolate. To reconcile these differences, the genome scale model was analyzed to determine the specific reactions that support cell growth. It was found that without glyoxylate carboligase, cell growth could theoretically be supported by the threonine pathway where oxaloacetate is converted to serine, homoserine and threonine. Threonine aldolase is capable of cleaving the amino acid to glycine for growth, and acetaldehyde for providing the acetyl-Coa necessary to replenish the acetyl-Coa that is consumed by malate synthase. Hence, it is the threonine metabolism generated from oxaloacetate that provides the route to support biomass in silico. This pathway converts acetyl-Coa to glycine. However, it is unlikely that these enzymes are expressed in sufficient quantities to carry enough flux to support growth. Hence, the primary role of the secondary malate synthase pathway and flux split in glyoxylate metabolism between the glyck2 and mals (malate synthase) reactions seems to be to replenish the TCA cycle intermediates as opposed to assimilating ethylene glycol.

A similar methodology was applied to determine the intracellular flux distribution under the micro-aerobic conditions. During the glycolate production phase (FIG. 4-5B), oxygen flowrate into the bioreactors was limited to create a micro-aerobic environment. The resulting drop in oxygen concentration affected the metabolic flux distribution. The most notable change was a reduction in the substrate uptake rate of ethylene glycol to ~0.7 mmol/gDW-hr, a quarter of what was observed during aerobic growth. Secondly, in silico simulations predicted reduced glyoxylate utilization through malate synthase and instead majority of the flux was diverted towards the TCA cycle through 2PG. Whereas the molar ratio of flux through lower glycolysis versus malate synthase was almost 1:1 under aerobic conditions, it was estimated to be 30:1 under micro-aerobic conditions. The decrease in the substrate uptake, it could be speculated, is likely caused by a lower oxidation rate of NADH by oxygen leading to an accumulation of reduced NAD co-factors and leaving fewer oxidized molecules available for ethylene glycol catabolism. The production of acetate in the metabolism is a characteristic of over-flow metabolism associated with fermentative metabolism. Trace amounts of formate, produced by pyruvate formate lyase which is transcriptionally controlled by oxygen is consistent with other studies showing activation of anaerobic pathways in the transition to a fermentative metabolism.

Figure 6A:
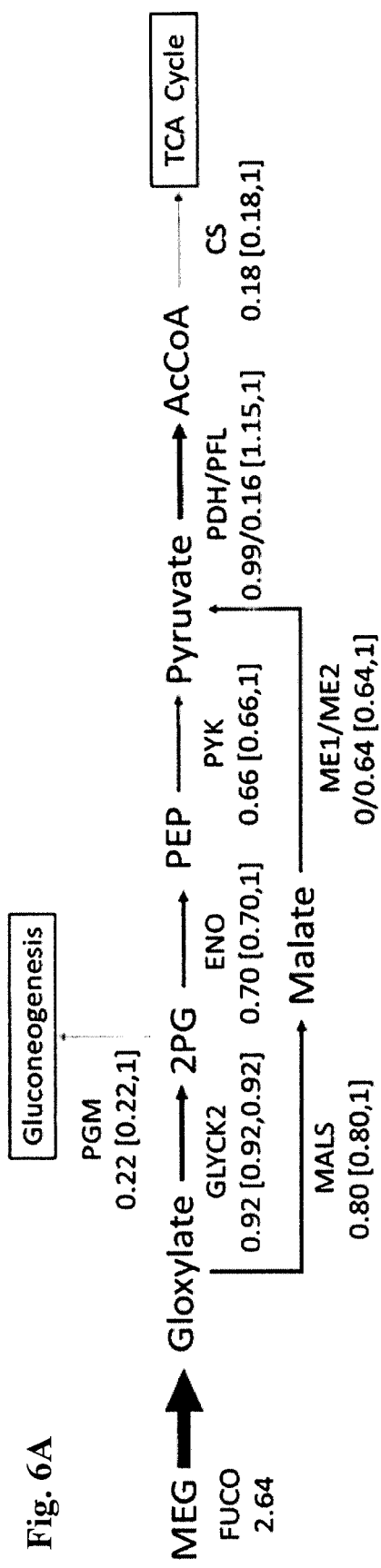
FIGS. 6A and 6B are diagrams showing flux distribution of the metabolism and enzymes in the pathway under aerobic (FIG. 6A) and oxygen limited (FIG. 6B) conditions.
Figure 6B:
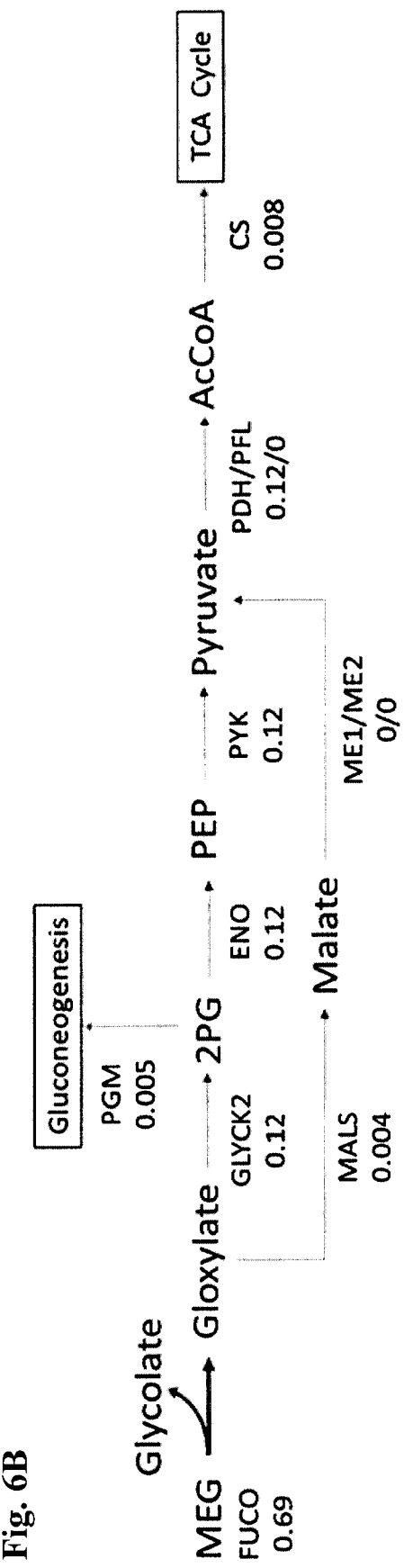

Regarding FIG. 6, it shows flux distribution of the metabolism and key enzymes in the pathway. Part (A) shows the estimated intracellular flux distribution under aerobic conditions. Part (B) shows under oxygen limiting conditions, the metabolic model estimates ethylene glycol flux ethylene glycol is primarily converted to glycolate. Values in brackets represent upper and lower values obtained from flux variability analysis. The flux ranges provide an estimate of the error in the reaction fluxes based on the constraints imposed for the above simulation. In this case, the relatively narrow ranges on the estimations are useful to attribute a physiologically meaningful interpretation to the data.

Use of Alternative Ethylene Glycol Oxidizing Enzymes Enables Ethylene Glycol Consumption Whereas it is shown herein that fucO and aldA can impart onto *E. coli* the ability for assimilating ethylene glycol as a carbon source, it is desired in some instances that an alternative to fucO be used when cells are grown under conditions of high aeration. This is because the FucO enzyme (and many other enzymes that use iron as a cofactor) contains an iron-sulphur cluster that is prone to inactivation in the presence of oxygen. Hence, several candidate enzymes that use zinc as a cofactor were tested and validated in vitro for their ability convert ethylene glycol to glycolaldehyde. One of the enzymes that was validated in vitro (the Gox0313 gene from *Gluconobacter oxydans*) was expressed in *Escherichia coli* MG1655, along with aldA on a low copy plasmid (p15A origin of replication). Cells were grown in M9 minimal media supplemented with 20 g/L ethylene glycol and 0.1% yeast extract in 250 mL shake flasks. Fermentation profiles of the strains confirm the ability to use Gox0313 for assimilating ethylene glycol. In comparison, the wild-type strain showed little growth resulting from the yeast extract present in the growth medium (see FIG. 9). In analyzing the results of this experiment, we observe it took 41 hours for cells to go from an OD600 of ~0.4 to ~9.9. By comparison, in an earlier experiment where a fucO variant with reduced sensitivity to oxygen was used, we observed that it took approximately 45 hours to go from an OD600 of ~0.4 to ~6.2. Thus, the Gox0313 containing variants reached a higher total biomass concentration over a shorter period of time relative to the fucO variants. Hence, these results suggest that this Zn containing enzyme is superior in its ability to support growth and ethylene glycol utilization over the fucO variants that contain an Fe cofactor.

DISCUSSION

Conventional approaches to the bio-based production of chemicals have relied on using glucose, and more recently xylose as feedstocks. Yet microorganisms tend to be very diverse in their ability to metabolize different carbon sources. In this work, the use of ethylene glycol as a substrate to replace glucose in bioprocesses for growth and chemical production was proposed and examined. Counter to other studies, many pertaining to the synthesis of ethylene glycol from glucose, our motivation for studying ethylene glycol as a substrate stems from the fact that it can also be derived from $CO_2^{6,31}$. Hence, its consideration as a feedstock that can potentially sequester carbon and lower greenhouse gas emissions is akin to studies examining syngas fermentation of formate utilization.

To assess ethylene glycol utilization in the context of biochemical production, glycolic acid production was examined. Glycolic acid is an alphahydroxy acid used in cosmetics and polymer applications. The results from our study allows us to conclude that ethylene glycol is a suitable platform for growth and highly efficient for producing glycolic acid. More generally it was found that with further metabolic engineering, ethylene glycol could be used to produce alcohols and other organic acids that are typically produced during fermentative metabolism. This capability, it is believed, can have an impact in industrial biotechnology. Elaboration on these findings is provided by examining three specific areas.

Consideration of ethylene glycol as a substrate can be driven by challenges related to the utilization of non-native substrates in *E. coli*. These interactions, which were described earlier as orthogonality, help to identify pathways with high and low degrees of interactions. Computationally, it was found that ethylene glycol exhibits a lower level of interactions than many natural and some synthetic pathways which can make it a more robust substrate than substrates such as formate or methanol. Hence, these interactions provided a rational basis for selecting and engineering a novel substrate utilizing pathway into *E. coli*. This work demonstrates the first de novo design of orthogonal pathway for metabolic engineering based on an orthogonality metric.

The results demonstrate the applicability of *E. coli* to use a new and novel substrate that has never been considered as a potential feedstock. Initial characterization of the cell growth determined that the substrate uptake rate was approximately 5 mmol/gDW-h. At typical cell densities for industrial processes (10-100 g/L)[24], this corresponds to net flux of 3-30 g/L-h, well above the required 3-4 g/L-h productivity for growth independent production typically needed[25]. Further characterization of these strains led us to determine that there was some oxygen sensitivity, especially during early exponential phase. It is believed that these are likely caused by metal catalyzed oxidation of FucO in the presence of excess aeration and could be addressed by using $O_2$-tolerant $Zn^{2+}$-dependent variants.

An important observation made during the course of these experiments was a reduction in the substrate uptake rate during oxygen limiting conditions. It is believed that the oxygen limitation results in increased NADH pools leading to a decrease in the rates of reaction catalyzed by fucO and aldA. This change in the rates had a net effect of lowering the flux of ethylene glycol into the cell. This finding necessitates a further study of cellular physiology under ethylene glycol utilization so as to understand the trade-off in yield and productivity as a function of the dissolved oxygen feeding in the bioreactor. For example, whereas increases were found in overall glycolate titres at 150 mL/min relative to 50 mL/min further, on-line monitoring in the fed-batch studies via maintaining a target respiratory quotient helped to increase product yields and titres at 50 mL/min relative to the earlier experimental conditions at 150 mL/min. Hence, optimization of aeration in the bioreactor would substantially improve economic performance, both in terms of product formation but also in terms of the absolute cost of aeration. For example, the operating conditions of the experiment in this bioreactor, correspond to a $k_L a$ of 120 $h^{-1}$. Typical jet loop bioreactors[26] are capable of delivering this design constraint at a mass transfer power of 3 $kW/m^3$. Therefore, a typical reactor that is 350 $m^3$ would consume 1000 kW of power or 160,000 kWh over the course of a typical fermentation. This requirement corresponds to an energy cost (at $0.10/kWh) of over $15,000 which represents 20%, a substantial fraction, of the final cost of the product at 100 g/L at $2/kg in a typical 350,000 L fermenter. Hence, the importance of optimizing process conditions through genetic engineering is important to its financial viability. Further work entailing a more detailed study of the oxygen transfer and glycolate titres is expected to more accurately determine the optimum conditions.

Further computational modelling allowed us to infer ratios of key branch points within the metabolism and identified glyoxylate carboligase as the central pathway for assimilating ethylene glycol, with malate synthase playing a relatively small role in its assimilation. Results of this modeling also showed that the much of the NADPH redox requirements for cell growth were surprisingly obtained through the pentose phosphate pathway and relatively little from the anaplerotic NADP dependent malic enzyme, as might be initially expected. It was also observed small amounts of acetate and trace amounts of ethanol in the fermentation media during microaerobic glycolate production phase. FBA modelling results predicted ethanol production during microaerobic conditions, but failed to predict acetate production, without the adequate constraints. The observation of acetate and ethanol in the fermentation medium, typical products of anaerobic growth suggest that microaerobic conditions may permit ethylene glycol as a suitable feedstock for the production of other anaerobic products despite its requirement for oxygen. Finally, by extending the observations from flux balance analysis, it was possible to use a process mass spec to measure in real-time the respiratory quotient and by use of a simple model, and show its applicability as parameter to control glycolic acid production during the course of the fermentation. This may open new opportunities for producing a variety of products using ethylene glycol as a feedstock provided the oxygen mass transfer rate can be efficiently controlled.

The results described herein establish a framework for future production of chemicals in *E. coli* using ethylene glycol as a substrate. Described herein, for the first time, is the successful production of glycolic acid from ethylene glycol using the substrate as a feedstock for growth and for production. A bioprocess based on ethylene glycol as a feedstock can have important implications and applications in the future for integrating biorefineries into industries where carbon dioxide can be captured from point sources, for example.

A central drawback of previous methods developed to date for converting ethylene glycol to glycolic acid is the method of production is reliant on a biotransformation that requires separation of the genetically modified microorganism and resuspension in a phosphate buffered media or distilled water. This presents a problem for commercial applications as it is expensive to separate biomass and suspend in a fresh medium. Hence it is desirous to develop a method for producing glycolic acid in a single fermentation vessel.

Whereas the production of glycolic acid by previous methods developed to date have relied on converting ethylene glycol in absence of nutrients or genes that allow for cell growth, new learnings disclosed in the present document for producing glycolic acid is that it is not necessary to limit cell growth either through the deactivation of the enzyme glycolate oxidase (glcDEF) or through the use of media that lacks one or more of the following: a carbon source for growth, a nitrogen source for growth, a phosphate source for growth, a sulfur source for growth, trace metals or vitamins required for growth. Furthermore, considering that both oxygen is necessary for growth and for glycolate production, it has not been shown in the past whether the presence of even small quantities of oxygen would allow for the production of glycolic acid since carbon could be diverted towards biomass. For this reason, the literature does not indicate that glycolic acid can be produced at yields greater than 80% by weight in a micro-aerobic environment and with a functioning glycolate oxidase. Further still, it is disclosed that when the oxygen uptake rate of the cell is less than 6 mmol/gDW/h the fermentation media is able to accumulate at least 80% by weight glycolic acid relative to the ethylene glycol consumed. In addition, whereas previously disclosed methods of glycolic acid production using a strain of *Escherichia coli* used a wild-type lactaldehyde reductase, we use an oxygen tolerant enzyme whose activity has been shown to be inhibitory in the presence of oxygen and the use of an oxygen tolerant alcohol reductase is a novel embodiment of a glycolic acid producing microorganism.

It is also noted that various alternative methods can be used adapted from the information described herein. For example, substrates other than ethylene glycol can in some cases be used as a carbon source, particularly those that are similar to ethylene glycol such as other diols or polyols where corresponding metabolic pathways are leveraged; microorganisms other than *E. Coli* can be used and can be genetically engineered in analogous ways as described herein, and the processes to use such microorganisms can be adapted in terms of optimizing operating conditions such as pH, temperature, and so on; other genetic modifications can be made in addition to those described herein; and other process operating conditions can be used depending on various factors (e.g., a threshold value for oxygen uptake rate other than 6 mmol/gDW/h can be used to define two process phases of growth and production; and/or a ratio of consumption of the substrate (e.g., ethylene glycol) in the two phases in terms of cell growth versus glycolate production; and/or other properties regarding the two phases and the possibility of additional phases prior to or after the two phases of growth and production). In addition, some aspects of the processes described herein can be used to produce other products, such as those similar to glycolate, or a mixture of products that may include glycolate, depending on various factors.

REFERENCES

1. Erickson, B., Nelson & Winters, P. Perspective on opportunities in industrial biotechnology in renewable chemicals. *Biotechnol. J.* 7, 176-185 (2012).
2. Jiang, Z., Xiao, T., Kuznetsov, V. L. & Edwards, P. P. Turning carbon dioxide into fuel. *Philos. Trans. A. Math. Phys. Eng. Sci.* 368, 3343-3364 (2010).
3. Liao, J. C., Mi, L., Pontrelli, S. & Luo, S. Fuelling the future: microbial engineering for the production of sustainable biofuels. *Nat. Rev. Microbiol.* 14, 288-304 (2016).
4. Siegel, J. B. et al. Computational protein design enables a novel one-carbon assimilation pathway. *Proc. Natl. Acad. Sci. U.S.A.* 112, 3704-9 (2015).
5. Bar-Even, A., Noor, E., Flamholz, A. & Milo, R. Design and analysis of metabolic pathways supporting formatotrophic growth for electricity-dependent cultivation of microbes. *Biochim. Biophys. Acta—Bioenerg.* 1827, 1039-1047 (2013).
6. Kuhl, K. P., Cave, E. R., Abram, D. N. & Jaramillo, T. F. New insights into the electrochemical reduction of carbon dioxide on metallic copper surfaces. *Energy Environ. Sci.* 5, 7050-7059 (2012).
7. Straub, M., Demler, M., Weuster-Botz, D. & Diirre, P. Selective enhancement of autotrophic acetate production with genetically modified *Acetobacterium woodii*. *J. Biotechnol.* 178, 67-72 (2014).
8. Shen, C. R. & Liao, J. C. Synergy as design principle for metabolic engineering of 1-propanol production in *Escherichia coli*. *Metab. Eng.* 17, 12-22 (2013).
9. Pirkov, I., Albers, E., Norbeck, J. & Larsson, C. Ethylene production by metabolic engineering of the yeast *Saccharomyces cerevisiae*. *Metab. Eng.* 10, 276-280 (2008).
10. Kortlever, R., Shen, J., Schouten, K. J. P., Calle-Vallejo, F. & Koper, M. T. M. Catalysts and Reaction Pathways for the Electrochemical Reduction of Carbon Dioxide. *J. Phys. Chem. Lett.* 6, 4073-4082 (2015).
11. Yang, N., Waldvogel, S. R. & Jiang, X. Electrochemistry of Carbon Dioxide on Carbon Electrodes. *ACS Appl. Mater. Interfaces* 8, 28357-28371 (2016).
12. Peterson, A. A., Abild-Pedersen, F., Studt, F., Rossmeisl, J. & Norskov, J. K. How copper catalyzes the electroreduction of carbon dioxide into hydrocarbon fuels. *Energy Environ. Sci.* 3, 1311 (2010).
13. Malik, K., Singh, S., Basu, S. & Verma, A. Electrochemical reduction of CO2 for synthesis of green fuel. *Wiley Interdiscip. Rev. Energy Environ.* e244 (2017). doi:10.1002/wene.244
14. Smanski, M. J. et al. Functional optimization of gene clusters by combinatorial design and assembly. *Nat. Biotechnol.* 32, 1241-1249 (2014).
15. Koivistoinen, O. M. et al. Glycolic acid production in the engineered yeasts *Saccharomyces cerevisiae* and *Kluyveromyces lactis*. *Microb. Cell Fact.* 12, 82 (2013).
16. Zahoor, A., Otten, A. & Wendisch, V. F. Metabolic engineering of *Corynebacterium glutamicum* for glycolate production. *J. Biotechnol.* 192, 366-375 (2014).
17. Adh, N. et al. Efficient utilization of pentoses for bioproduction of the renewable two-carbon compounds ethylene glycol and glycolate. *Nucleic Acids Res.* 7, 80-87 (2013).
18. Cam, Y. et al. Engineering of a Synthetic Metabolic Pathway for the Assimilation of (d)-Xylose into Value-Added Chemicals. *ACS Synth. Biol.* 5, 607-618 (2016).
19. Alkim, C. et al. The synthetic xylulose-1 phosphate pathway increases production of glycolic acid from xylose-rich sugar mixtures. *Biotechnol. Biofuels* 9, 201 (2016).
20. Deng, Y., Mao, Y. & Zhang, X. Metabolic engineering of *E. coli* for efficient production of glycolic acid from glucose. *Biochem. Eng. J.* 103, 256-262 (2015).
21. Kataoka, M., Sasaki, M., Hidalgo, A. G. D. & Nakano, M. Glycolic Acid Production Using Ethylene Glycol-Oxidizing Microorganisms. 8451, 37-41 (2014).
22. Gao, X., Ma, Z., Yang, L. & Ma, J. Enhanced Bioconversion of Ethylene Glycol to Glycolic Acid by a Newly Isolated *Burkholderia* sp. EG13. *Appl. Biochem. Biotechnol.* 174, 1572-1580 (2014).
23. Wei, G. et al. High cell density fermentation of *Gluconobacter oxydans* DSM 2003 for glycolic acid production. *J Ind. Microbiol. Biotechnol.* 36, 1029-1034 (2009).
24. Gibson, D. G. et al. Enzymatic assembly of DNA molecules up to several hundred kilobases. *Nat. Methods* 6, 343-345 (2009).
25. Toraya, T., Honda, S. & Fukui, S. Fermentation of 1,2-propanediol with 1,2-ethanediol by some genera of 25. Enterobacteriaceae, involving coenzyme B12-dependent diol dehydratase. *J. Bacteriol.* 139, 39-47 (1979).
26. Child, J. & Willetts, A. Microbial metabolism of aliphatic glycols bacterial metabolism of ethylene glycol. *BBA—Gen. Subj.* 538, 316-327 (1978).
27. Hartmanis, M. G. & Stadtman, T. C. Diol metabolism and diol dehydratase in *Clostridium glycolicum. Arch. Biochem. Biophys.* 245, 144-152 (1986).
28. Miickschel, B. et al. Ethylene glycol metabolism by *Pseudomonas putida. Appl. Environ. Microbiol.* 78, 8531-8539 (2012).
29. Boronat, A., Caballero, E. & Aguilar, J. Experimental evolution of a metabolic pathway for ethylene glycol utilization by *Escherichia coli. J. Bacteriol.* 153, 134-139 (1983).
30. Lu, Z. et al. Evolution of an *Escherichia coli* Protein with Increased Resistance to Oxidative Stress *. 273, 8308-8316 (1998).
31. Tamura, J. et al. Electrochemical reduction of CO2 to ethylene glycol on imidazolium ion-terminated self-assembly monolayer-modified Au electrodes in an aqueous solution. *Phys. Chem. Chem. Phys.* 17, 26072-26078 (2015).
32. Method for producing high amount of glycolic acid by fermentation. US 20120315682 A1
33. Eukaryotic cell and method for producing glycolic acid. US 20140295510 A1
34. Process for producing hydroxycarboxylic acid. U.S. Pat. No. 8,728,780 B2
35. Glycolic Acid Production By Fermentation From Renewable Resources. WO 2007/141316 A2
36. Direct conversion of sugars to glycolic acid. WO 2016193540 A1
37. Microbial Preparation Of Glycolic Acid. JPS54119089 (A)
38. Production Of Glycolic Acid By Microorganism. JPH10174594 (A)
39. Production Of Glycolic Acid By Yeast. JPH10174593 (A)
40. Production of polyhydroxyalkanoates from polyols. US 20020164729 A1.
41. Fermentation process for producing glycolic acid. US 20120178136 A1
42. Levin et al., "The ternary complex of *Pseudomonas aeruginosa* alcohol dehydrogenase with NADH and ethylene glycol". *Protein Science* (2004), 13(6): 1547-1556.
43. Isobe, "Oxidation of Ethylene Glycol and Glycolic Acid by Glycerol Oxidase". *Bioscience, Biotechnology, and Biochemistry* (1995), 59(4): 576-81.
44. Isobe and Nishiseb, "A new enzymatic method for glycolaldehyde production from ethylene glycol". *Journal of Molecular Catalysis B: Enzymatic.* (1995), 1(1): 37-43.
44. Muckschel et al., "Ethylene Glycol Metabolism by *Pseudomonas putida*" *Appl. Environ. Microbiol.* (2012), 78(24): 8531-8539.
45. Brouns et al., "Identification of the Missing Links in Prokaryotic Pentose Oxidation Pathways". *The Journal of Biological Chemistry* (2006), 281(37): 27378-27388.
46. Klein et al., "A novel dye-linked formaldehyde dehydrogenase with some properties indicating the presence of a protein-bound redox-active quinone cofactor". *Biochem. J* (1994) 301, 289-295.
47. Zhang et al., "Enhancement of cell growth and glycolic acid production by overexpression of membrane-bound alcohol dehydrogenase in *Gluconobacter oxydans* DSM 2003". *Journal of Biotechnology.* (2016), 237(10): 18-24.
48. Gaston and Stadtman, "Fermentation of ethylene glycol by *Clostridium glycolicum*, sp. N". *J Bacteriol.* (1963), 85:356-62.
49. Kishi et al., "Heterotrophic utilization of ethylene glycol and propylene glycol by *Chlorella protothecoides*". *Algal Research* (2015), 11: 428-434.
50. Kataoka et al., "Glycolic acid production using ethylene glycol-oxidizing microorganisms". *Biosci. Biotechnol. Biochem.* (2001), 65: 2265-2270.

The references mentioned in the present document are hereby incorporated herein by reference.

The invention claimed is:

1. A fermentation process for producing glycolate, as a product or intermediate, from ethylene glycol, wherein said process comprises a growth phase and a production phase, wherein said process comprises:
   supplying a fermentation broth into a fermentation vessel, the fermentation broth comprising ethylene glycol and a microorganism having a functional metabolic pathway for utilizing ethylene glycol as a carbon source in the presence of oxygen, wherein the functional metabolic pathway comprises polypeptides that catalyze (a) conversion of ethylene glycol to glycolaldehyde, (b) conversion of glycolaldehyde to glycolate, and (c) conversion of glycolate to glyoxylate;
   providing aeration conditions during the growth phase to culture the microorganism at an oxygen uptake rate (OUR) promoting biomass accumulation and limiting accumulation of glycolate until a desired level of biomass is reached; and
   adjusting aeration conditions during the production phase to culture the microorganism at an OUR that is lower than the OUR in the growth phase, thereby limiting biomass accumulation and promoting accumulation of glycolate,
   wherein the conversion of glycolate to glyoxylate in the microorganism is catalyzed by glycolate oxidase in an oxygen-utilizing reaction, wherein the OUR in the growth phase is maintained sufficiently high to promote the microorganism to utilize glyoxylate for biomass accumulation and the OUR in the production phase is maintained sufficiently low to disrupt the conversion of glycolate to glyoxylate, thereby promoting accumulation of glycolate,
   wherein:
   (i) the polypeptide that catalyzes (a) is an alcohol dehydrogenase that uses an oxygen-insensitive cofactor, wherein the oxygen-insensitive cofactor is zinc;
   (ii) the polypeptide that catalyzes (b) is a lactaldehyde dehydrogenase encoded by the *Escherichia coli* aldA gene; and
   (iii) the polypeptide that catalyzes (c) is glycolate oxidase.

2. The fermentation process of claim 1, wherein the OUR in the growth phase is sufficiently high to inhibit extracellular accumulation of glycolate in the fermentation broth.

3. The fermentation process of claim 1, wherein the OUR in the production phase is sufficiently low to inhibit metabolic conversion of glycolate into a downstream metabolite.

4. The fermentation process of claim 1, wherein the OUR in the growth phase, in the production phase, or in both the growth phase and the production phase, is between 4 mmol/gDW/h and 8 mmol/gDW/h, wherein the OUR in the production phase is lower than the OUR in the growth phase.

5. The fermentation process of claim 1, wherein the OUR in the growth phase is greater than 6 mmol/gDW/h, and the OUR is the production phase is below 6 mmol/gDW/h.

6. The fermentation process of claim 1, wherein the OUR in the growth phase is greater than the OUR is the production phase by at least 0.5 mmol/gDW/h, by at least 1 mmol/gDW/h, by at least 2 mmol/gDW/h, by at least 3 mmol/gDW/h, by at least 4 mmol/gDW/h, or by at most 4 mmol/gDW/h.

7. The fermentation process of claim 1, wherein the growth phase and the production phase occur in the same fermenter vessel and/or fermentation broth.

8. The fermentation process of claim 1, wherein the microorganism is a bacterium.

9. The fermentation process of claim 8, wherein the bacterium is *Escherichia coli*.

10. The fermentation process of claim 1, wherein the alcohol dehydrogenase that uses zinc as a cofactor is a zinc-dependent alcohol dehydrogenase.

11. The fermentation process of claim 1, wherein the alcohol dehydrogenase that uses zinc as a cofactor is a cinnamyl alcohol dehydrogenase.

12. The fermentation process of claim 1, wherein the enzyme alcohol dehydrogenase that uses zinc as a cofactor is encoded by the *Gluconobacter oxydans* 621H GOX0313 gene.

* * * * *